(12) United States Patent
Zhou et al.

(10) Patent No.: US 8,765,454 B2
(45) Date of Patent: Jul. 1, 2014

(54) FLUIDIC DEVICES AND METHODS FOR MULTIPLEX CHEMICAL AND BIOCHEMICAL REACTIONS

(76) Inventors: Xiaochuan Zhou, Houston, TX (US); Xiaollan Gao, Houston, TX (US); Erdogan Gulari, Ann Arbor, MI (US)

(*) Notice: Subject to any disclaimer, the term of this patent is extended or adjusted under 35 U.S.C. 154(b) by 1820 days.

(21) Appl. No.: 10/589,860

(22) PCT Filed: Feb. 18, 2005

(86) PCT No.: PCT/US2005/005389
§ 371 (c)(1), (2), (4) Date: Dec. 4, 2008

(87) PCT Pub. No.: WO2005/080606
PCT Pub. Date: Sep. 1, 2005

(65) Prior Publication Data
US 2011/0143964 A1    Jun. 16, 2011

Related U.S. Application Data

(60) Provisional application No. 60/545,435, filed on Feb. 18, 2004.

(51) Int. Cl.
*C12Q 1/68* (2006.01)
*C12M 1/34* (2006.01)
*B01L 3/00* (2006.01)

(52) U.S. Cl.
USPC ...... 435/287.2; 435/6.1; 435/288.5; 422/502; 422/507

(58) Field of Classification Search
None
See application file for complete search history.

(56) References Cited

U.S. PATENT DOCUMENTS

| | | | | |
|---|---|---|---|---|
| 6,235,471 | B1* | 5/2001 | Knapp et al. | 435/6.19 |
| 6,858,185 | B1* | 2/2005 | Kopf-Sill et al. | 422/504 |
| 2002/0012616 | A1* | 1/2002 | Zhou et al. | 422/130 |
| 2002/0037499 | A1* | 3/2002 | Quake et al. | 435/5 |
| 2003/0120035 | A1* | 6/2003 | Gao et al. | 530/333 |
| 2003/0138819 | A1* | 7/2003 | Gong et al. | 435/6 |
| 2005/0053979 | A1* | 3/2005 | Livak et al. | 435/6 |

FOREIGN PATENT DOCUMENTS

DE    19810499    * 9/1999

* cited by examiner

*Primary Examiner* — Betty Forman
(74) *Attorney, Agent, or Firm* — G Kenneth Smith

(57) ABSTRACT

The present invention describes microfluidic devices that provide novel fluidic structures to facilitate the separation of fluids into isolated, pico-liter sized compartments for performing multiplexing chemical and biological reactions. Applications of the novel devices including biomolecule synthesis, polynucleotide amplification, and binding assays are also disclosed.

16 Claims, 12 Drawing Sheets

FLUIDIC DEVICES AND METHODS FOR MULTIPLEX CHEMICAL AND BIOCHEMICAL REACTIONS

This application claims the benefit of U.S. Provisional Application No. 60/545,435, filed on Feb. 18, 2004.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates to the field of fluidic devices for carrying out multiplex chemical or biochemical reactions and for performing multiplex chemical and/or biochemical assays. More particularly, this invention relates to devices and methods for distributing fluids into a plurality of compartments for carrying out multiplex chemical and/or biochemical reactions, and detecting a plurality of chemical and/or biochemical compounds.

2. Description of Related Art

Modern drug development, disease diagnosis, pathogen detection, gene discovery, and various genetic-related technologies and research increasingly rely on making, screening, and assaying a large number of chemical and/or biochemical compounds. Traditional methods of making and examining the compounds one at a time are becoming increasingly inadequate. Therefore there is a need for chemical/biochemical reaction systems and devices to perform high-throughput assay and synthesis.

One of the most commonly used high-throughput multiplexing method relies on the use of titer plates. Each titer plate contains 96, 384, or 1,536 microwells or microtubes in which individual chemical and/or biochemical reactions are carried out. (need a reference) In a standard format the reaction media inside individual microwells or microtubes are physically isolated from each other. Chemical and biochemical reagents are delivered into the microwells or microtubes either robotically or manually using pipettes or dispensers. In a standard format the distances between adjacent microwells or microtubes are 9.0 mm, 4.5 mm, and 2.25 mm for 96, 384, and 1,536 microwell titer plates, respectively. To increase throughput, higher densities of the microwells are needed.

Another multiplexing method relates to microarrays. The most well-known microarray is DNA microarray, which, in its most common form, is a glass plate containing a two-dimensional array of DNA materials on its surface. A DNA microarray is used as a multiplexing detection device. Each element of the array has a unique DNA sequence, which is used to specifically recognize or detect a unique complementary DNA sequence in a sample solution. The element density of a DNA microarray is usually much higher than that of a titer plate. On a commercially available DNA microarray the distance between two adjacent elements is between 10 micrometer and 500 micrometer. DNA microarray, are rapidly becoming fundamental tools in genomic, proteomic, and other biological research (Fodor et al. Science 251, 767 (1991), Schena et al. Science 270, 467 (1995) and "The Chipping Forecast II" Nat. Genet. 32 (2002)). In addition to research use, DNA microarray has the potential to be used as a clinical diagnostic tool (Carr et al. Nat. Oncogene. 22, 3076 (2003) and "Microarrays in Cancer: Research and Applications" BioTechniques Supplement March 2003). In addition to DNA microarray there are various other types of microarrays, such as peptide microarray, protein microarray, and tissue microarray, for various research and diagnostic applications (Gao et al. Nature Biotechnol. 20, 922 (2002)).

Microarray technology has fundamentally changed the way of studying biological systems from observing one or a few genes or molecular species at a time to observing pathways, networks, and molecular machines that involve the interplay of a large collection of genes and pools of molecules. DNA microarray chips available today operate based on the hybridization of target DNA or RNA molecules (the sample to be tested) in a solution phase with probe DNA (oligonucleotides or cDNA) molecules immobilized on solid substrates, which are mostly in either plate or bead forms (Rubenstein in BioTechniques Supplement March 2003). The hybridization results are used in monitoring gene expression, determining nucleotide sequences, identifying gene mutations, detecting pathogens, and selecting and measuring activities of ligand molecules such as peptides, proteins, antibiotics and other organic and inorganic molecules.

In spite of the usefulness of the currently available DNA microarrays, their performance is far from being satisfactory for many applications. Inadequate assay specificity is one of a multitude of limitations with the current DNA microarray methodology, which are fundamentally associated with the single-pair hybridization assay, i.e. with results determined by the hybridization of only one pair of nucleotide molecules. Assay specificity relies on hybridization discrimination, which in turn is determined by probe (immobilized DNA) sequence design, probe sequence purity, target (sample DNA) sequence composition, and hybridization conditions. Selection of hybridization probes is a complex issue, particularly for gene expression applications, in which samples contain tens of thousands genes. Shorter oligo probes should theoretically provide higher hybridization discrimination but they tend to have poor hybridization properties leading to lower sensitivity, not to mention the difficulty of finding short unique sequences in large genomes (Shchepinov et al. Nucleic Acids Res. 25, 1155 (1997) and Hughes et al. Nat. Biotechnology, 19, 342 (2001)). As oligo probes become longer, the hybridization discrimination decreases, although detection sensitivity increases and it is easier to find unique sequences in large genomes. It has been found that when the probe length reaches 35, it needs to have at least 3 mismatches to reliably discriminate different target DNA sequences by hybridization. This fundamental problem of limited specificity has lead to different results from chips of different venders and technology platforms (Kuo et al. Bioinformatics 18, 405 (2002)).

Today's DNA microarrays are not suitable for quantitative measurement. This will likely become one of the roadblocks to hinder the technology from being used as a clinical diagnostic tool, although technological efforts have been made to address this problem (Dudley et al. Proc. Natl. Acad. Sci. 99, 7554 (2002)). Studies have shown a significant compression of differential ratios (ratios of hybridization intensities from different samples) in microarray data as compared to real-time PCR (Polymerase Chain Reaction) data. Real-time PCR has been established as the most commonly used and accepted standard for validating DNA microarrays in gene expression use (Chuaqui et al. Nat. Genet. 32 Supplement 509 (2002)). According to the published data, while about 70% of array results of highly differentiated genes were qualitatively consistent with real-time PCR, consistent validation was not achieved for genes showing less than a four-fold change on the array. For many of the genes examined, significant quantitative differences were found between array- and real-time-PCR-based data (Mangalathu et al. Journal of Molecular Diagnostics 3, 26 (2001)). For these reasons, array users often choose for further study only those genes with the highest differential expression ratios. This strategy can easily overlook genes of significant interest. Obviously, it is highly desirable to develop a more robust and quantitative array platform in order to reach a level of confidence for which relatively small differences in gene expression between samples are real and that genes showing such differences are worth further investigation.

The third limitation of today's DNA microarray is detection sensitivity. The single-pair hybridization assay used in the DNA microarray does not involve any amplification and requires a fairly large amount of sample. For example, in gene expression applications with most of the commercial array products, 2 to 5 microgram of total RNA sample is needed for each assay. However, some of the clinical biopsy tissue samples yield less than 1 microgram of total RNA sample. For pathogen detection, microarrays are considered not sensitive enough without the aid of PCR (Call et al. J Microbiol Methods 53, 235 (2003)). Amplification of either DNA or RNA samples during sample preparation has been used to boost the amount of samples before they are applied to array chips (Lockhart et al. Nature Biotech. 14, 1675 (1996)). This method, however, causes concerns for altering ratios of the genes involved.

The challenges of specificity, accuracy, and sensitivity mentioned above can be solved using real-time PCR. Higuchi et al. first demonstrated fluorescence monitoring kinetic PCR amplification process in real-time (Higuchi et al. Biotechnology 10, 413 (1992)). The method has been developed into a powerful tool, often referred as a golden standard, for quantitative measurement of nucleic acids with various applications, including gene expression, pathogen detection, and SNP (Single Nucleotide Polymorphism) detection. Due to its reduced detection time and simplification of quantification, the method is believed to potentially have the greatest impact on the general public in environmental monitoring and nucleic acid diagnostics (Walker, Science 296, 557 (2002)).

A real-time PCR system detects PCR products as they accumulate during a PCR reaction process. There are several variations of detection systems. The most well-known and popular system is Taqman system (Heid et al. Genome Res. 6, 986 (1996)). A pair of PCR primers and one fluorescence resonance energy transfer (FRET) probe are used in the detection of each target sequence. The FRET probe is a short oligonucleotide complementary to one of the strands of the target sequence. Each FRET probe contains a reporter dye and a quencher dye. Taq polymerase is used. If the target sequence is present, the probe anneals downstream from the forward primer site and is cleaved by the 5' nuclease activity of Taq DNA polymerase as this primer is extended. The cleavage of the probe separates the reporter dye from quencher dye, increasing the reporter dye signal and allowing primer extension to continue to the end of the template strand. Additional reporter dye molecules are cleaved from their respective probes with each cycle, causing an increase in fluorescence intensity proportional to the amount of amplicon produced.

Real-time PCR assay is intrinsically highly specific. For one target sequence to be detected, it has to contain all three sequence segments complementary to a detection probe, a forward primer, and a reverse primer, respectively. Any errors produced by one event will likely be filtered out by the other two events. For example, if in one event a forward primer happened to prime to a wrong sample sequence and produced a wrong amplicon, this wrong amplicon will likely either not be recognized by the detection probe or not be further amplified by the reverse primer. In comparison, today's DNA microarrays rely on the hybridization of only one pair of nucleotides and do not have any build-in error-checking mechanism. Even with the multiple-probe approach, such as the one used by Affymetrix (www.affymetrix.com), the assay specificity is not increased in any way and the improvement is only in the reduction of the statistical variance of the data. The benefit of this approach is derived by averaging the results of hybridization of multiple individual probes, which hybridize directly with sample sequences and have no relationship with the hybridization events of any other probes that are designed to target at the same sample sequence or same gene.

Real-time PCR assay is highly sensitive and is quantitative. PCR is an exponential amplification process. In principle, PCR can pick up and amplify a single copy of a target sequence. As a daily practice for RNA detection, real-time PCR requires nanograms of RNA samples as compared to micrograms required by today's DNA microarrays. Moreover, the ability of real-time PCR to quantitatively measure the copy numbers of target sequences in samples is non-existent in today's DNA microarray technology.

Most of existing instruments perform PCR reactions in either 96- or 384-well titer plates. Samples are manually or robotically pipetted into individual wells. Applied Biosystems recently started the sale of a Micro Fluidic Card in a 384-well format (www.appliedbiosystems.com). The new card offers the advantages of reduced consumption of samples and reagents and the elimination of labor-intensive pipetting steps. The new card has the same area size as that of conventional 96- and 384-well titer plates. However, its fluidic design and the operational principle fundamentally limit it from being able to achieve the degree of miniaturization and the level of area density that have demonstrated in DNA microarrays (U.S. Pat. No. 6,272,939).

There have been an increasing number of reports of the development of micro-fabricated PCR devices, including continuous flow and microwell devices made from silicon or plastic materials (Kopp et al. Science 280, 1046 (1998), Nagai et al. Anal. Chem. 73, 1043 (2001), and Yang et al. Lab on a Chip, 2, 179 (2002)). A low-energy consumption and fast thermal cycling silicon-chip-based real-time PCR detection system for field use was also demonstrated (Belgrader et al. Science, 284, 449 (1999)). There are also reports of performing DNA microarray assays using PCR as a sample preparation process involving microfabricated array chips (U.S. Pat. No. 6,448,064). O'Keefe et al disclosed a method for conducting multiple simultaneous micro-volume chemical and biochemical reactions on an array of micro-holes as described in United States Patent Application Publication 2001/0055765 A1. The method is said to be able to perform real-time PCR among several other applications.

For research and many other applications, it is highly desirable to have a flexible way of multiplex synthesis of microarrays of various molecules, including nucleic acids and peptides, and to perform assays of various sequences in a short turn-around time. Gao et al. in U.S. Pat. No. 6,426,184 described a method of combining PGR (photogenerated reagent) chemistry, micromirror array projector, and microwell plates to achieve flexible and highly parallel synthesis of microarrays of varieties of molecules. The teaching of which is incorporated herein by reference. In a separate disclosure, PCT WO 0202227, Zhou described a microfluidic device that has the features of dynamic isolation for performing parallel chemical synthesis using PGR chemistry with improved process robustness. The teaching of the disclosure is also incorporated herein by reference. For the purpose of performing real-time PCR and certain other biochemical assays in a microarray format and in a highly multiplexing scale, it is desirable or even necessary to have a build-in static isolation mechanism in a microarray device in addition to a flexible chemical synthesis capability for implementing biochemical probes.

An objective of this invention is to provide microfluidic devices for performing multiplex chemical and biochemical reactions. Another objective of this invention is to provide highly flexible method of implanting a plurality of chemical and/or biochemical molecules into the microfluidic devices. Yet another objective of this invention is to provide methods of multiplex biochemical assays using the microfluidic devices. A further objective of this invention is to provide systems for performing parallel chemical and biochemical assay analysis, including real-time PCR, ELISA (enzyme linked-immunosorbent assay) and other assays.

BRIEF SUMMARY OF THE INVENTION

1. A microfluidic reaction device comprising:
(a) a plurality of chambers having a first conduit and a second conduit;
(b) a first transport channel having a first end, said first transport channel having a bypass channel at said first end, said first transport channel being in flow communication with at least one said chamber through connection with said first conduit;
(c) a second transport channel having a first end, said second transport channel having a bypass channel at said first end, said second transport channel being in flow communication with at least one said chamber through connection with said second.

2. A method for amplifying target nucleic acid comprising:
(a) attaching an oligonucleotide to a solid support within a chamber, the oligonucleotide comprising a first primer, a second primer and a binding probe sequence wherein the first primer, second primer and binding probe sequences are separated from one another and the solid support by a cleavable linker;
(b) incubating a target nucleic acid with the oligonucleotide under conditions in which complementary target sequence and binding probe sequence hybridize to one another;
(c) washing the chamber;
(d) adding a solution comprising a cleavage substance, polymerase, dNTPs, and divalent cation to the chamber such that the first primer, second primer and binding probe sequence are released from one another and from the solid support so that the first primer, second primer, binding probe sequence, target nucleic acid, polymerase, dNTPs and divalent cation produce a reaction mixture within the chamber;
(e) subjecting the reaction mixture to two or more cycles of heating and cooling such that the target nucleic acid is amplified.

3. A method for amplifying a plurality of target nucleic acids on a microarray wherein the microarray is comprised of a plurality of separate chambers comprising:
(a) attaching an first oligonucleotide to a solid support within a first chamber, the oligonucleotide comprising a first primer, a second primer and a first binding probe sequence wherein the first primer, second primer and binding probe sequences are separated from one another and the solid support by a cleavable linker;
(b) attaching a second oligonucleotide to a solid support within a second chamber, the second oligonucleotide comprising a third primer, a fourth primer and a second binding probe sequence wherein the third primer, fourth primer and second binding probe sequences are separated from one another and the solid support by a cleavable linker;
(c) incubating a target nucleic acid comprising two or more nucleic acid sequences with the first and second oligonucleotide under conditions in which complementary target nucleic acid sequences and binding probe sequences hybridize to one another;
(d) washing the chamber;
(e) adding a solution comprising a cleavable substance, polymerase, dNTPs, and divalent cation to the first and second chamber such that the first primer, second primer, third primer, fourth primer, first binding probe sequence and second binding probe sequence are released from one another and from the solid support so that the first primer, second primer, first binding probe sequence, target nucleic acid, polymerase, dNTPs and divalent cation produce a first reaction mixture within the first chamber and the third primer, fourth primer, second binding probe sequence, target nucleic acid, polymerase, dNTPs and divalent cation produce a second reaction mixture within the second chamber;
(f) subjecting the first and second reaction mixture to two or more cycles of heating and cooling such that a plurality of target nucleic acids are amplified.

4. A method for amplifying target nucleic acid comprising:
(a) synthesizing an oligonucleotide to a solid support within a chamber, the oligonucleotide comprising a first primer, a second primer and a binding probe sequence wherein the first primer, second primer and binding probe sequences are separated from one another and the solid support by a cleavable linker;
(b) incubating a target nucleic acid with the oligonucleotide under conditions in which complementary target sequence and binding probe sequence hybridize to one another;
(c) washing the chamber;
(d) adding a solution comprising a cleavage substance, polymerase, dNTPs, and divalent cation to the first and second chamber such that the first primer, second primer, and the binding probe sequence are released from one another and from the solid support so that the first primer, second primer, the binding probe sequence, target nucleic acid, polymerase, dNTPs and divalent cation produce a reaction mixture within the chamber;
(e) subjecting the reaction mixture to two or more cycles of heating and cooling such that the target nucleic acid is amplified.

5. A method for amplifying a plurality of target nucleic acids on a microarray wherein the microarray is comprised of a plurality of separate chambers comprising:
(a) synthesizing a first oligonucleotide to a solid support within a first chamber, the oligonucleotide comprising a first primer, a second primer and a first binding probe sequence wherein the first primer, second primer and first binding probe sequence are separated from one another and the solid support by a cleavable linker;
(b) attaching a second oligonucleotide to a solid support within a second chamber, the second oligonucleotide comprising a third primer, a fourth primer and a second binding probe sequence wherein the third primer, fourth primer and second binding probe sequence are separated from one another and the solid support by a cleavable linker;
(c) incubating a target nucleic acid comprising two or more nucleic acid sequences with the first and second oligonucleotide under conditions in which complementary target nucleic acid sequences and binding probe sequences hybridize to one another;

(d) washing the chamber;

(e) adding a solution comprising a cleavage substance, polymerase, dNTPs, and divalent cation to the first and second chamber such that the first primer, second primer, third primer, fourth primer, first binding probe sequence and second binding probe sequence are released from one another and from the solid support so that the first primer, second primer, first binding probe sequence, target nucleic acid, polymerase, dNTPs and divalent cation produce a first reaction mixture within the first chamber and the third primer, fourth primer, second binding probe sequence, target nucleic acid, polymerase, dNTPs and divalent cation produce a second reaction mixture within the second chamber;

(f) subjecting the first and second reaction mixture to two or more cycles of heating and cooling such that a plurality of target nucleic acids are amplified.

6. A method for amplifying target nucleic acid comprising:

(a) attaching a first primer, a second primer and a binding probe sequence to a solid support such that the first primer, second primer and binding probe sequence is attached to the solid support within a chamber such that when treated with a cleavage substance the first primer, second primer and binding probe sequence are released from the solid support;

(b) incubating a target nucleic acid with the oligonucleotide under conditions in which complementary target sequence and binding probe sequence hybridize to one another;

(c) washing the chamber;

(d) adding a solution comprising a cleavage substance, polymerase, dNTPs, and divalent cation to the chamber such that the first primer, second primer and binding probe sequence are released from the solid support so that the first primer, second primer, binding probe sequence, target nucleic acid, polymerase, dNTPs and divalent cation produce a reaction mixture within the chamber;

(e) subjecting the reaction mixture to two or more cycles of heating and cooling such that the target nucleic acid is amplified.

7. A method for amplifying target nucleic acid comprising:

(a) synthesizing a first primer, a second primer and a binding probe sequence to a solid support such that the first primer, second primer and binding probe sequence are attached to the solid support within a chamber such that when treated with a cleavage substance the first primer, second primer are released from the solid support;

(b) incubating a target nucleic acid with the oligonucleotide under conditions in which complementary target sequence and binding probe sequence hybridize to one another;

(c) washing the chamber;

(d) adding a solution comprising a cleavage substance, polymerase, dNTPs, and divalent cation to the chamber such that the first primer and second primer are released from the solid support so that the first primer, second primer, binding probe sequence, target nucleic acid, polymerase, dNTPs and divalent cation produce a reaction mixture within the chamber;

(e) subjecting the reaction mixture to two or more cycles of heating and cooling such that the target nucleic acid is amplified.

8. A method for amplifying a plurality of target nucleic acids on a microarray wherein the microarray is comprised of a plurality of separate chambers comprising:

(a) attaching a first primer, a second primer and a first binding probe sequence are attached to the solid support within a first chamber such that when treated with a cleavable substance the first primer and second primer are released from the solid support;

(b) attaching a third primer, a fourth primer and a second binding probe sequence are attached to the solid support within a second chamber such that when treated with a cleavage substance the third primer and fourth primer are released from the solid support;

(c) incubating a target nucleic acid comprising two or more nucleic acid sequences with the first and second binding probe sequences under conditions in which complementary target nucleic acid sequences and binding probe sequences hybridize to one another;

(d) washing the chamber;

(e) adding a solution comprising a cleavage substance, polymerase, dNTPs, and divalent cation to the first and second chamber such that the first primer, second primer, third primer and fourth primer are released from the solid support so that the first primer, second primer, target nucleic acid, polymerase, dNTPs and divalent cation produce a first reaction mixture within the first chamber and the third primer, fourth primer, target nucleic acid, polymerase, dNTPs and divalent cation produce a second reaction mixture within the second chamber;

(f) subjecting the first and second reaction mixture to two or more cycles of heating and cooling such that a plurality of target nucleic acids are amplified.

9. A method for amplifying a plurality of target nucleic acids on a microarray wherein the microarray is comprised of a plurality of separate chambers comprising:

(a) synthesizing a first primer, a second primer and a first binding probe sequence is attached to the solid support within a first chamber such that when treated with a cleavage substance the first primer and second primer are released from the solid support;

(b) attaching a third primer, a fourth primer and a second binding probe sequence is attached to the solid support within a second chamber such that when treated with a cleavage substance the third primer and fourth primer are released from the solid support;

(c) incubating a target nucleic acid comprising two or more nucleic acid sequences with the first and second binding probe sequences under conditions in which complementary target nucleic acid sequences and binding probe sequences hybridize to one another;

(d) washing the chamber;

(e) adding a solution comprising a cleavage substance, polymerase, dNTPs, and divalent cation to the first and second chamber such that the first primer, second primer, third primer, fourth primer and first binding probe sequence are released from the solid support so that the first primer, second primer, target nucleic acid, polymerase, dNTPs and divalent cation produce a first reaction mixture within the first chamber and the third primer, fourth primer, target nucleic acid, polymerase, dNTPs and divalent cation produce a second reaction mixture within the second chamber;

(f) subjecting the first and second reaction mixture to two or more cycles of heating and cooling such that a plurality of target nucleic acids are amplified.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Definition of Terms

Figure 1A:
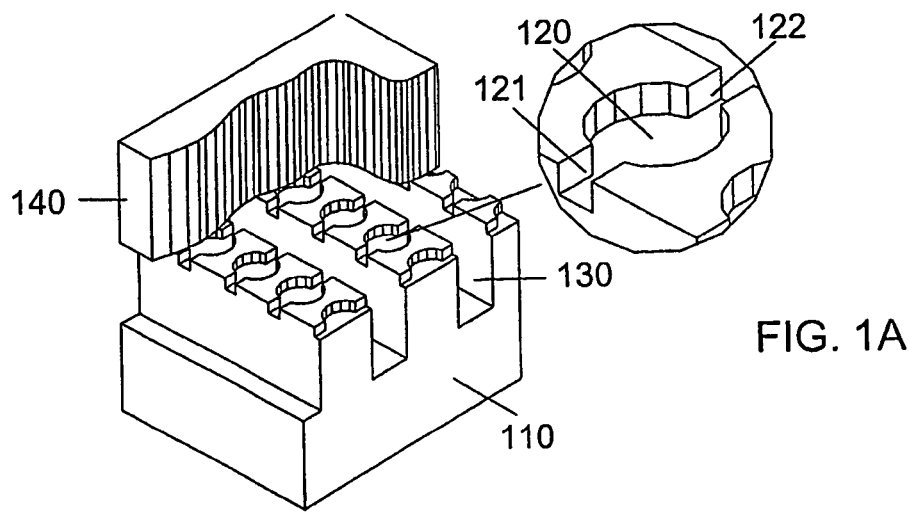
FIG. 1A is an exploded perspective view of a chamber array device.

The term "photogenerated-reagent precursor" (PRP) refers to a chemical compound that produces one or more reactive chemical reagents when it is irradiated or illuminated with photons of certain wavelengths. The wavelengths may be in any appropriate regions of infrared, visible, ultraviolet, or x-ray.

The term "photogenerated-acid precursor" (PGAP) refers to a chemical compound that produces acids when it is irradiated or illuminated with photons of certain wavelengths. The wavelengths may be in any appropriate regions of infrared, visible, ultraviolet, or x-ray.

The term "photogenerated-acid" (PGA) refers to an acid that is produced from PGAP under irradiations or illuminations with photons of certain wavelengths. The wavelengths may be in any appropriate regions of infrared, visible, ultraviolet, or x-ray.

The term "photogenerated reagent". (PGR) refers to a chemical compound that is produced from the irradiation or illumination of a photogenerated-reagent precursor. In most of the cases, PGR is a reactive reagent in the concerned chemical or biochemical reactions. However, the term may be used to refer to any chemical compounds that are derived from the irradiation of the photogenerated reagent precursor and may or may not be reactive in certain chemical/biochemical reactions.

The term "probe molecule" refers to a ligand molecule that is employed to bind to other chemical entities and form a larger chemical complex so that the existence of said chemical entities could be detected. Preferably, within a suitable window of chemical and physical conditions, such as pH, salt concentration, and temperature, the probe molecule selectively bind to other chemical entities of specific chemical sequences, specific conformations, and any other specific chemical or physical properties.

The term "fluid" refers to a liquid or a gas material.

The term "chamber" refers to a three-dimensional hollow structure that is surrounded by walls of one or more materials. The shape of a chamber may take any forms, include but not limited to cylinder, cube, tube, disk, sphere, hemisphere, or any other regular or irregular three-dimensional forms. A chamber may contain one or more openings.

The term "aqueous solution" refers to a water solution. The aqueous solution may contain various solutes including but not limited to organic or inorganic salts, organic or inorganic acids, organic or inorganic bases, enzymes, proteins, nucleic acids, surfactants, and other organic or inorganic molecules.

The term "oil" refers to a liquid that is immiscible or substantially immiscible with water. The oil may be selected from various materials including but not limited to perfluoro compounds, liquid fluorinated parafins, liquid chlorinated parafins, liquid chloro-fluoro hydrocarbon compounds, hydrocarbon compounds, silicon oil, mineral oil, and liquid wax. The term "oil" may also refers to liquid that is immiscible or substantially immiscible with water and can be converted into a solid or a gel form by polymerization or any other appropriate chemical reactions.

The term "fluidic structure" refers to a structure that is constructed or used for handling or directing fluids. A fluidic structure may contain one or more basic components, including but not limited to channels, pipes, slits, chambers, conduits, and holes of various sizes. A fluidic structure may be made of one or more materials selected from various rigid as well as flexible substrate materials, including but not limited to glass, plastic, silicon, and elastomer.

The term "biological molecules" refers to molecules of biological importance including but not limited to nucleic acids, peptides, proteins, antibodies, enzymes, and antibiotics.

The present invention provides a novel method and fluidic structures to form a plurality of isolated chambers for the performance of multiplex chemical and biochemical reactions. FIG. 1A is an exploded perspective view of a chamber array device that embodies one aspect of the present invention. The device is made of a fluidic template 110, on which fluidic structures are fabricated, and a cover plate 140, which is bonded to the fluidic template 110. The fluidic structures include chambers 120, entrant conduits 121, exit conduits 122, and transport channels 130. The sizes, materials, and the relations of the various parts of the disclosed device will become clear as the individual components and the operations of the device are described.

Figure 1B:
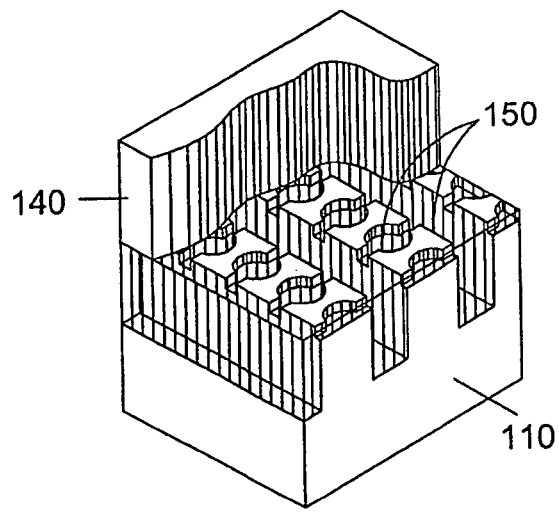
FIG. 1B is an exploded perspective view of a chamber array device of FIG. 1A that is filled with the first fluid inside chambers as well as transport channels.
Figure 1C:
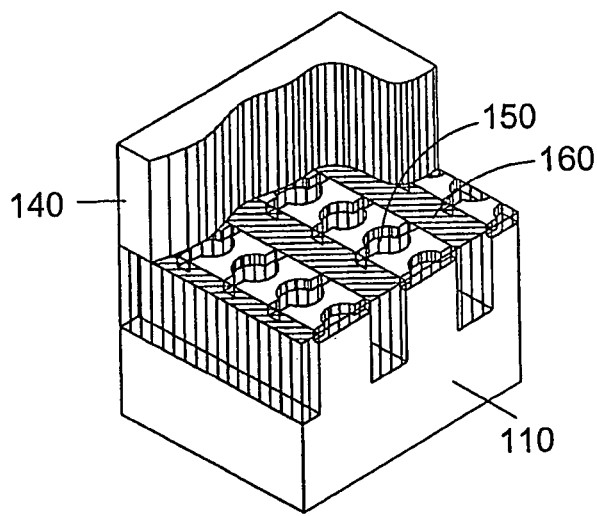
FIG. 1C is an exploded perspective view of a chamber array device that is filled the first fluid inside chambers and the second fluid inside transport channels.

FIG. 1B and FIG. 1C illustrate the operation process of the disclosed device. In the first step, the first fluid 150 is sent into the device to fill the chambers 120 and transport channels 130, as shown in FIG. 1B. In the next step, the second fluid 160, which is immiscible or substantially immiscible with the first fluid, is sent into the device to selectively replace the first fluid 150 in the transport channels 130 while leaving the first fluid 150 in the chambers 120, as shown in FIG. 1C. As result, the first fluid 150 is confined or isolated inside chambers 120. The principle and the embodiment fluidic structures to facilitate the selective replacement will be described and become clear in the following paragraphs of this disclosure.

In a preferred embodiment of the present invention, the first fluid 150 and the second fluid 160 do not or substantially do not chemically interact with each other and immiscible or substantially immiscible with each other. In a one aspect of the present invention, the first fluid 150 is an aqueous solution and the second fluid 160 is oil. The aqueous solution may contain various solutes including but not limited to organic or inorganic salts, organic or inorganic acids, organic or inorganic bases, enzymes, proteins, nucleic acids, surfactants, and other organic or inorganic molecules. The oil may be selected from various materials including but not limited to perfluoro compounds, hydrocarbon compounds, silicon oil, mineral oil, and liquid wax. In another aspect of the present invention, the first fluid 150 is an aqueous solution and the second fluid 160 is gas. In yet another aspect of the present invention, the first fluid 150 is oil and the second fluid 160 is an aqueous solution. In yet another aspect of the present invention, the first fluid 150 is oil and the second fluid 160 is gas. In yet another aspect of the present invention, the first fluid 150 is gas and the second fluid 160 is an aqueous solution. In yet another aspect of the present invention, the first fluid 150 is gas and the second fluid 160 is oil. Obviously, many more combinations of immiscible fluids can be selected to achieve the isolation of the first fluid 150 inside chambers 120. For example, an aqueous solution and mercury can be selected as the first fluid 150 and the second fluid 160, respectively.

Figure 1D:
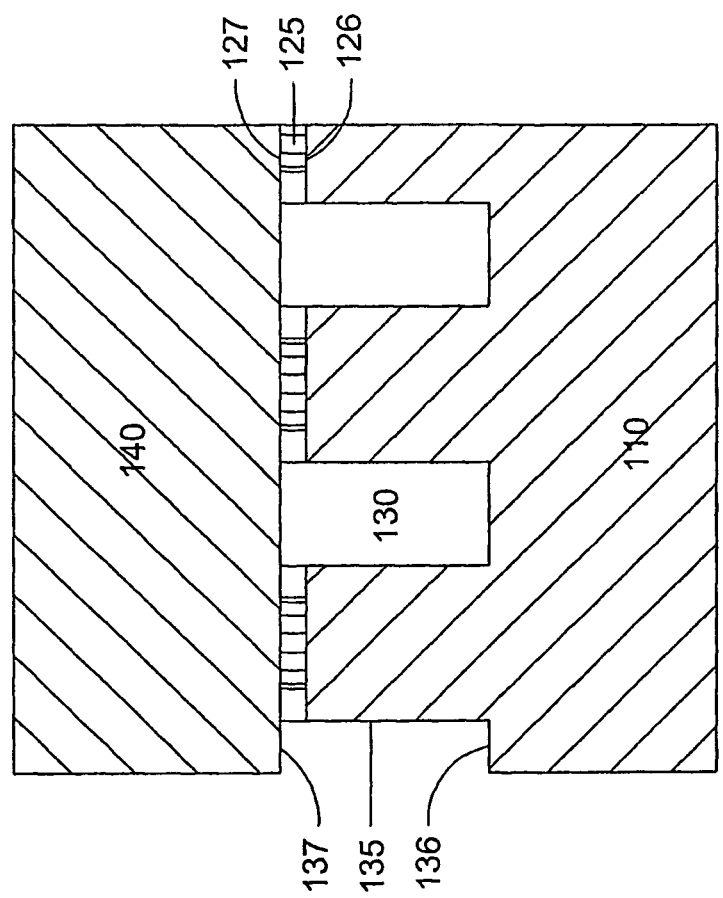
FIG. 1D is a cross-section view of the chamber array device shown in FIG. 1A.

In a preferred embodiment of the present invention, the interior surfaces of chambers 120 and transport channels 130, shown in FIG. 1A, are coated with films of different affinities. For example, when it is desirable to confine an aqueous solution inside chambers 120, it is preferred to coat the interior surfaces of the chamber 120, including upper surface 127, lower surface 126, and side surface 125 of FIG. 1D, with a hydrophilic film while coat the interior surfaces of transport channels 130, including upper surface 137, lower surface 136, and side surface 135 of FIG. 1D, with a hydrophobic film. On the other hand, when it is desirable to confine an oil solution inside chambers 120, it is preferred to coat the interior surfaces of the chamber 120 with a hydrophobic film while coat the interior surfaces of transport channels 130 with a hydrophilic film.

Figure 2A:
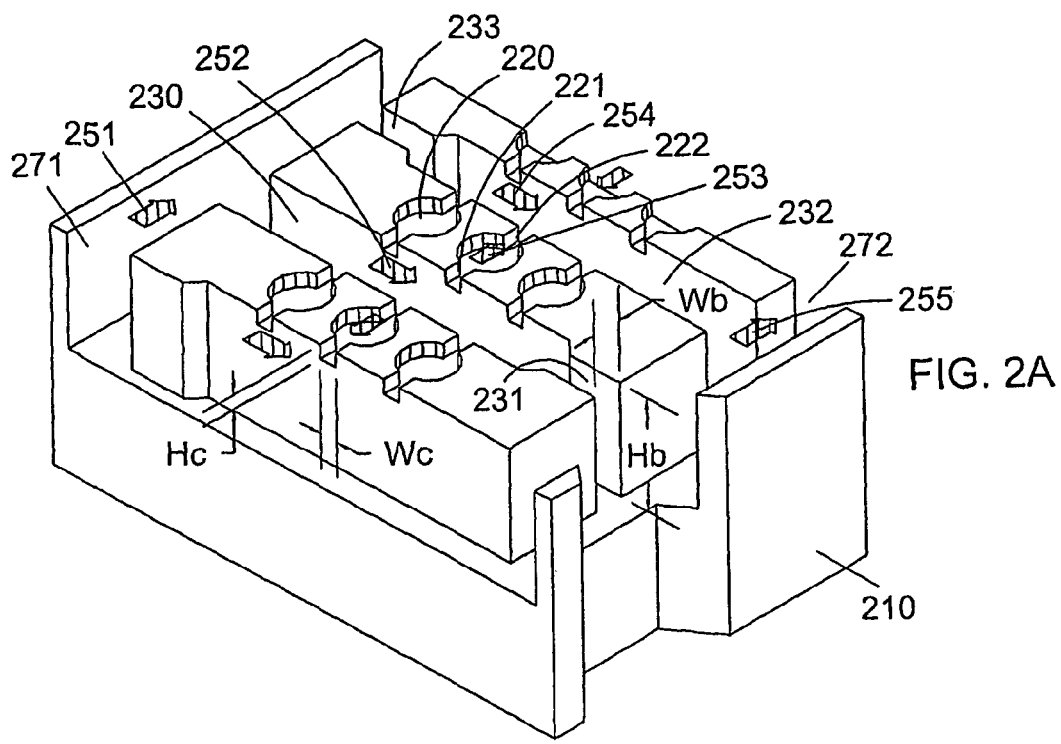
FIG. 2A is an exploded perspective view of a chamber array device containing bypass channels that embodies the present invention.
Figure 2B:
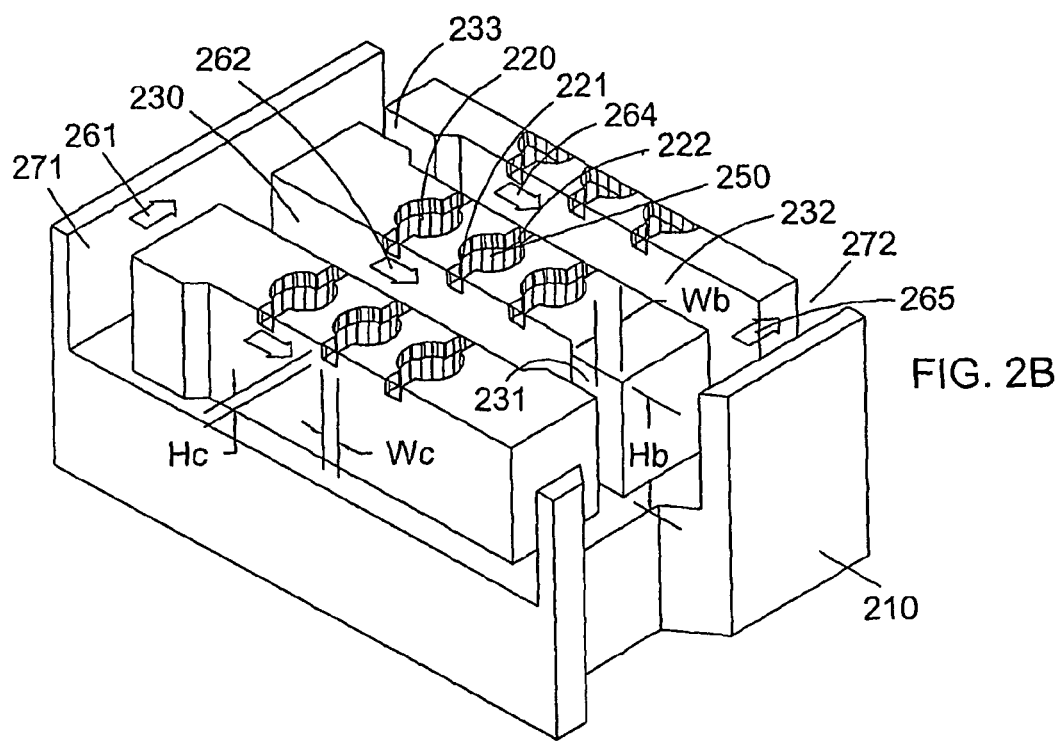
FIG. 2B schematically illustrates the flow path of the second fluid in the chamber array device of FIG. 2A.

FIG. 2A and FIG. 2B schematically illustrate the structure and operation of an exemplary fluidic device embodiment of the present invention. These drawings reveal the fluid template 210 portion of the device and omit a cover plate for the purpose of visual clarity. Referring to FIG. 2A, when the first fluid is injected into the device, it flows along an inlet distribution channel 271 as an inlet stream 251, splits into branch streams 252 through inlet transport channels 230, further splits into chamber streams 253 through entrance conduit 221, chambers 220, and exit conduit 222, merges into branch stream 254 in outlet transport channels 232, further merges into outlet stream 255 in outlet distribution channel 272, and flows out the device. A part of branch stream 252 passes through a bypass channel 231 to merge into outlet stream 255 without passing through any chamber 220. A portion of the first fluid 251 in the distribution channel 271 passes through bypass channel 233 to flow through the outlet transport channel 232 and makes up a part of the branch stream 254. In one aspect of the present invention, the fluidic structures of the fluidic device of FIG. 2A are symmetric so that inlet and outlet of the device can be switched without affecting fluid flow characteristics except the reversal of flow directions. In the most preferred embodiment of the present invention, the cross-section area of the bypass channels 231 and 233 is significantly larger than that of the inlet conduit 221 of the chambers 220.

FIG. 2B illustrates the flow of the second fluid through the fluidic device of the present invention. For explanation purpose, we assume that the first fluid 250 is an aqueous solution and has already filled the fluidic device before the second fluid is injected into the fluidic device. We further assume that the interior surfaces of chambers 220 are hydrophilic. Under these assumptions, in a preferred embodiment of the present invention the second fluid is either a gas or oil and the interior surfaces of fluid channels are hydrophobic. When the second fluid is injected into the fluidic device, under an appropriate flow rate, it enters the inlet distribution channel 271 as an inlet stream 261. A portion of the inlet stream 261 flows into an inlet transport channel 230 to become a branch stream 262, which passes through an bypass channel 231 and merges into an outlet stream 265 in an outlet channel 272. Another portion of the inlet stream 261 passes through a bypass channel 233 and flows along an outlet transport channels 233 as a branch stream 264 and then merges into the outlet stream 265 in the outlet channel 272. During this process the second fluid pushes the first fluid out of the fluidic device everywhere except chambers 220. As a result, the first fluid is isolated inside the chambers 220.

The operational principle of the fluidic device of this invention is based on pressure barriers at the junctions of cross section change. Assume a channel having a hydrophilic internal surface, a cross-sectional area of A, a wetted perimeter of L, and is filled with water. According to Shaw in "Introduction to Colloid and Surface Chemistry" Butterworths, London, 1983, the minimum pressure required to push air into this channel is estimated by $P=\gamma \times L/A$, where $\gamma=72.8$ mN/m is the surface tension of water at water/air interface. As shown in FIG. 2B and FIG. 2A, the wetted perimeters through the inlet conduit 221 of a chamber 220 and through a bypass channel 231 of the inlet transport channel 230 are $L_c=2(W_c+H_c)$ and $L_b=2(W_b+H_b)$, respectively. $W_c$, $W_b$ and $H_c$, $H_b$, are the width and the height of inlet conduit 221 and bypass channel 231, respectively. The corresponding cross-sectional areas are $A_c=W_c \times H_c$ and $A_b=W_b \times H_b$, respectively. For explanation purpose, we assume that $W_c=28$ μm, $H_c=14$ μm, $W_b=48.5$ μm, $H_b=150$ μm. We then derive that the minimum pressures for air to push through the inlet conduit 221 and the bypass channel 231 are $P_c=2.26$ psi and $P_b=0.57$ psi, respectively. Therefore, as long as we send in an air with a pressure between 0.57 psi and 2.26 psi we will push water out of the inlet transport channel 230 through bypass channel 231 but not chamber 220 through inlet conduit 221. We call this pressure range as operational pressure window. Obviously, it is desirable to have a wide operational pressure window. We also assume that bypass channel 233 has the same cross section dimensions as that of bypass channel 231 so that in the same pressure range air would pass through the bypass channel 233 and push water out of the outlet transport channel 232. As result, water is isolated by air on both inlet and outlet sides of the chamber 220. The above analysis is based on a simplified calculation to serve the purpose of explaining principles. More elaborated calculations are available such as the one by Man et al. in "Microfabricated capillarity-driven stop valve and sample injector", at 1998 MEMS Conference, Heidelberg, Germany, Jan. 25-29, 1998.

Based on the principle that are described above, those skilled in the art of fluidics are able to perform calculations to estimate the operation conditions and to vary fluidic structures to achieve the isolation of fluid inside chambers when different fluids are used. Calculations relating to fluidic flow through fluidic structures that are coated with films of different affinities are also well known to those skilled in the art (Man et al. in "Microfabricated plastic capillary systems with photodefinable hydrophilic and hydrophobic regions", at the 1999 Transducers Conference, Sendai, Japan, Jun. 7-10, 1999).

Figure 3:
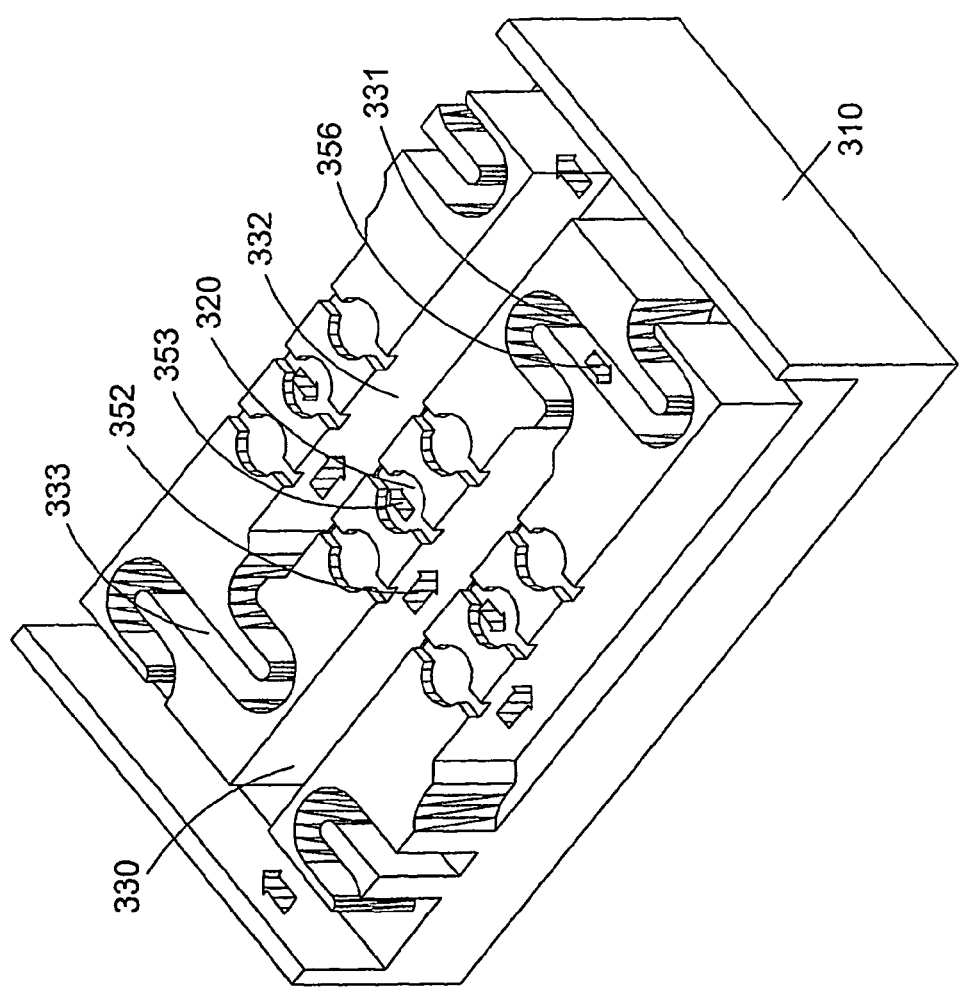
FIG. 3 is an exploded perspective view of a chamber array device containing serpentine-shaped bypass channels that embodies the present invention.

FIG. 3 shows another preferred fluidic device embodiment of the present invention. Serpentine-shaped bypass channels 331 are utilized so that the total length of the bypass channels 331 can be adjusted to achieve a suitable ratio between the amounts of fluid 353 flowing through chambers 320 and fluid 356 flowing through the bypass channels 331 while minimizing the size of the fluidic device. For many assay applications of the fluidic device of this invention, some of which are described in later sections of this disclosure, it is desirable to maximize the flow through the chambers 320 or to minimize the flow through the bypass channels 331. On the other hand, as described in the above paragraphs, it is desirable for the bypass channels 331 to have reasonably large cross-section areas so as to obtain a wide operational pressure window. Therefore, it is often desirable to increase the total length of the bypass channels 331 in order to increase flow resistance so as to reduce the flow through the bypass channels 331 while using a reasonably large cross-section area for the bypass channels 331. The calculation of fluid flow in a fluidic network, such as the fluidic device of this invention, is a well-known art to those skilled in the art of fluid dynamics.

Figure 4A:
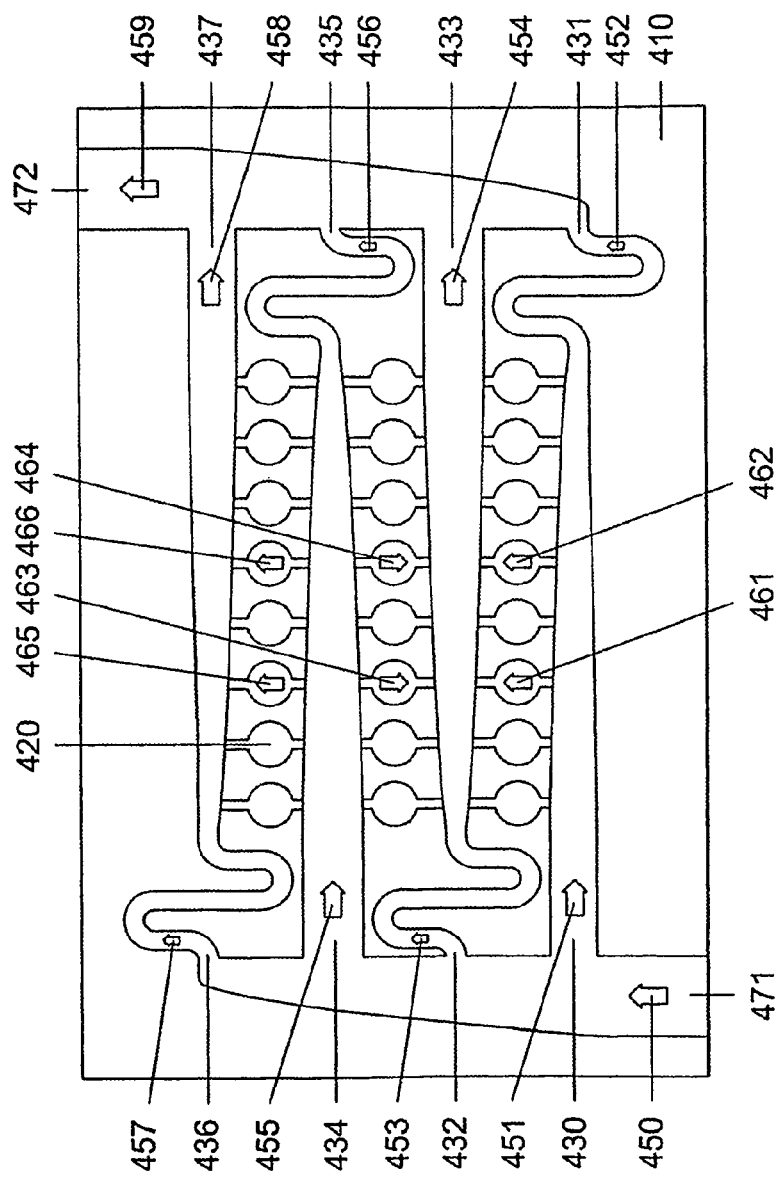
FIG. 4A is a schematic diagram of a fluidic device containing tapered channels.

FIG. 4A shows a schematic diagram of another preferred fluidic device embodiment of the present invention. In this embodiment, fluidic channels are shaped in such a way that predetermined flow rate distributions across the fluidic channels and chambers 420 are obtained. For example, it is often desirable to have a uniform flow across all chambers 420. In case of the fluidic device shown in FIG. 4A, this means that the volume flow rates of chamber streams 461, 462, 463, 464, 465, and 466 are identical or approximately identical. This invention achieves this by using tapered fluid channels as shown in FIG. 4A. The shapes of the tapered inlet distribution channel 471 and outlet distribution channel 472 are designed to distribute a fluid into and out of transport channels 451, 455, 454, and 458 according to predetermined ratios. In one exemplary design, the volume flow rate of stream 455 equals to that of stream 454, the volume flow rate of stream 451 equals that of 458, and the volume flow rate of stream of 451 is half of that of steam 454. The shapes of the transport channels 430, 433, 434, and 437 are designed to produce uniform volume flow rate across all chambers 420.

Figure 4B:
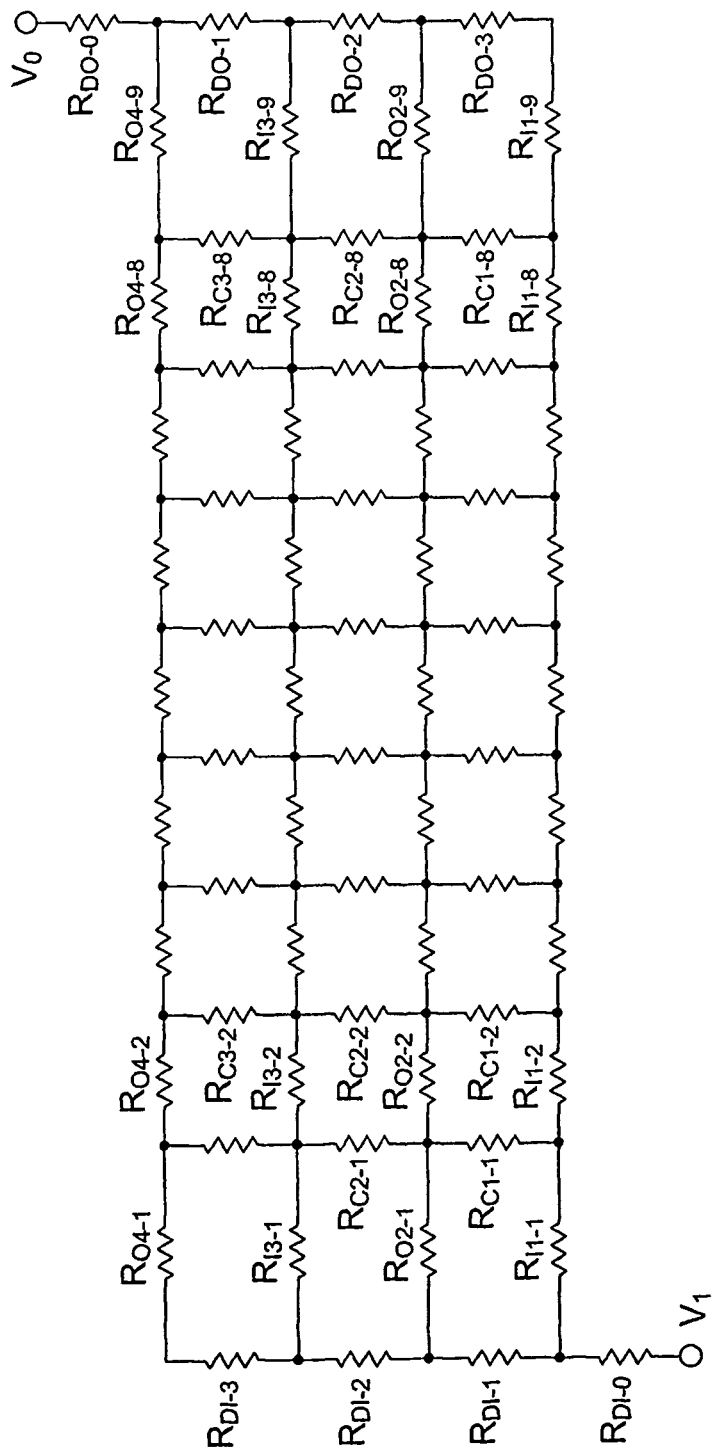
FIG. 4B is a resistor network model of the fluidic network shown in FIG. 4A.

For a given fluid flow distribution, the shapes of fluid channels can be designed based on fluidic dynamic calculation and/or mathematical modeling which are well-known to those skilled in the art of fluidics. One simple and effective modeling approach is resistor network calculations. This approach is valid under steady state laminar flow conditions. FIG. 4B shows a resistor network model of the fluidic device of FIG. 4A. Each resistor represents one segment of the fluidic structure. For example, resistors $R_{I1-1}$, $R_{I1-2}$ to $R_{I1-8}$ of FIG. 4B make up the inlet transport channel 430 of FIG. 4A. Resistor $R_{I1-9}$ of FIG. 4B represents the bypass channel 431 of FIG. 4A. $R_{C1-1}$, $R_{C1-2}$, and $R_{Ci-j}$ (where i=1 to 3 and j=1 to 8) of FIG. 4B represent chambers 420 of FIG. 4A. The resistance is defined as the ratio of pressure drop and volume flow rate. The calculation of pressure drop through various fluidic structures, such as rectangle channel, slab, and pipe, is familiar to those skilled in the art of fluid dynamics and can be found in literature such as the one by White "Fluid Mechanics", 3rd ed. John Wiley and Sons, (1994) and the references therein. For a given flow condition, for example an equal volume flow rate through resistors $R_{Ci-j}$ for i=1 to 3 and j=1 to 8 R, a set of simultaneous linear equations are established. More than one solution may be derived by solving the equations when the number of unknowns is more than the number of equations, meaning that more than one set of fluidic structural parameters can be used to achieve the same basic fluid flow condition, such as uniform flow through all chambers 420 of FIG. 4A. With additional conditions, such as fixing the values of $R_{I3-9}$, forcing $R_{I3-9}=R_{O2-1}$, $R_{I3-8}=R_{O2-2}$, . . . , $R_{I1-9}=2R_{I3-9}$, $R_{I1-8}=2R_{I3-8}$, . . . , a unique solution can be found, from which the shapes of the inlet and outlet transport channels 430, 434, 433, and 437 of FIG. 4A are derived. Obviously, following the above teaching, those skilled in the art can design fluidic structures to achieve predetermined flow distributions other than uniform flow across chambers 420 of FIG. 4A. Commercial computational fluidic dynamic software packages, such as FLUENT from Fluent Inc., New Hampshire, USA and CFD-ACE from CFD Research Corporation, Alabama, USA, are available and can be used for simulating fluid flow so as to help the design of fluidic structures of the present invention.

To further improve the ability to achieve a predetermined flow distribution, a designer of the disclosed device needs to take the variation and characteristics of fabrication processes into consider. For example, a reactive ion etching (RIE) process for producing high-aspect-ratio features tends to produce different etching depths for features with different feature sizes and/or different feature densities (Madou, M., Fundamentals of Microfabrication: The Science of Miniaturization, Second Edition, CRC Press, New York, (2002)). As a result, a taper channel, when made by RIE process, may have a varying depth along the channel. In most cases, the narrowing the channel cross-section is the shallower the channel depth will be produced. In a preferred design practice, an iteration process is used. In the first round of the iteration process, a device is designed, fabricated, and feature size and depth profiles are measured. The measurement may be done using various tools, such as SEM (scanning electron microscope), 3D optical profiler, step meter, which are well know to those skilled in the art of microfabrication. The measurement result can be used as a feedback for the adjustment of design. For example, the fabrication-dependent depth variation along a tapered channel can be compensated by adjusting the width profile of the channel to achieve a predetermined flow resistant profile.

The actual flow distribution inside a fluidic device can be experimentally measured using various tracing and profiling methods that are well established in the field of fluidics. For example, microspheres may be suspended into a liquid of close density and flow into the disclosed device. The flow distribution inside the device can be mapped out by following the movement of individual particles using a microscope coupled with a high-speed camera. The result of flow distribution measurement can be used as a feedback for the adjustment of design. The number of required design-fabricationmeasurement iterations depends on specific fabrication and measurement methods involved and on the tolerance specified. In many applications requiring a uniform flow distribution, a flow rate variation within 10% among all chambers is sufficient. For other applications a 20% variation is acceptable. And yet for other applications a 5% or less variation might be required.

Figure 5A:
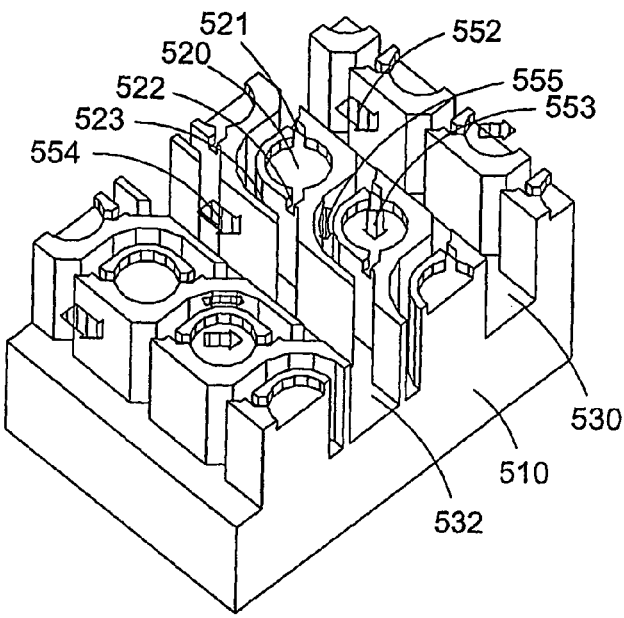
FIG. 5A is an exploded perspective view of a chamber array device containing side bypass channels that embodies the present invention.
Figure 5B:
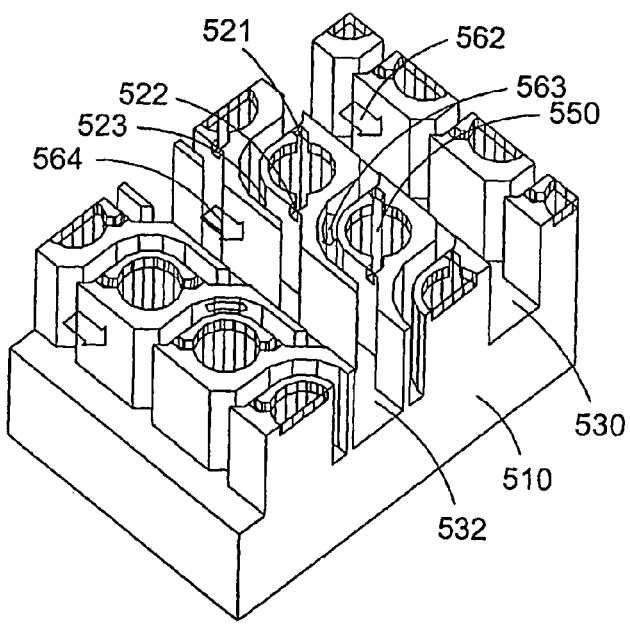
FIG. 5B schematically illustrates the flow path of the second fluid in the chamber array device of FIG. 5A.

FIG. 5A and FIG. 5B illustrate the structure and operation of yet another preferred fluidic device embodiment of the present invention. Key fluidic structures of this device include chambers 520, inlet transport channels 530, outlet transport channels 532, and bypass channels 522. This embodiment differentiates from the one shown in FIG. 2A and FIG. 2B in the arrangement of bypass channels. As shown in FIG. 5A, in this fluidic device embodiment each chamber 520 is surrounded by a bypass channel 523 while the fluidic device shown in FIG. 2A the bypass channels 231 and 233 are placed at the end of the inlet and outlet transport channels 230 and 232. However, the operation principles of the two embodiments are similar. In a preferred embodiment, the across-section area of the bypass channel 523 is substantially larger than that of the inlet conduit 521 of chamber 520.

To operate the fluidic device of FIG. 5A, the first fluid is initially sent into the fluidic device through an inlet distribution channel (not shown in FIG. 5A). The first fluid splits into branch streams 552 and flow along inlet transport channels 530, further splits and flows through bypass channels 523 and through inlet conduits 521, chambers 520, and outlet conduits 522, and merges into branch streams 554 in outlet transport channels 532, and eventually merges into an outlet distribution channel (not shown in FIG. 5A) and exits the fluidic device. Referring to FIG. 5B, after the fluidic device is filled with the first fluid 550, the second fluid, which is immiscible with the first fluid 550, is sent into the fluidic device. The second fluid splits into branch streams 562 and flows along the inlet transport channels 530; it further splits, flows through bypass channels 523, and merges into branch streams 564 in the outlet channels 532. The second fluid would not pass through the inlet conduit 521 under the following preferred conditions. First, the first fluid 550 is an aqueous solution. Second, the interior surface of the chambers 520 is hydrophilic. Third, the second fluid is either a gas or oil. Forth, the across-section area of the bypass channel 523 is substantially larger than that of the inlet conduit 521. Fifth, the interior surface of inlet transport channel 530, bypass channel 523, and outlet channel 532 are hydrophobic. Additionally, the flow rate of the second fluid needs to be sufficiently low so that the pressure drop between the junctions of inlet conduit 521 and the outlet conduit 523 at the bypass channel 523 is lower than a surface-tension induced pressure barrier at the entrance cross-section of the inlet conduit 521. As result, the first fluid 550 is isolated inside the chambers 520. The flow directions of either the first or the second fluid can be in either direction.

Figure 6A:
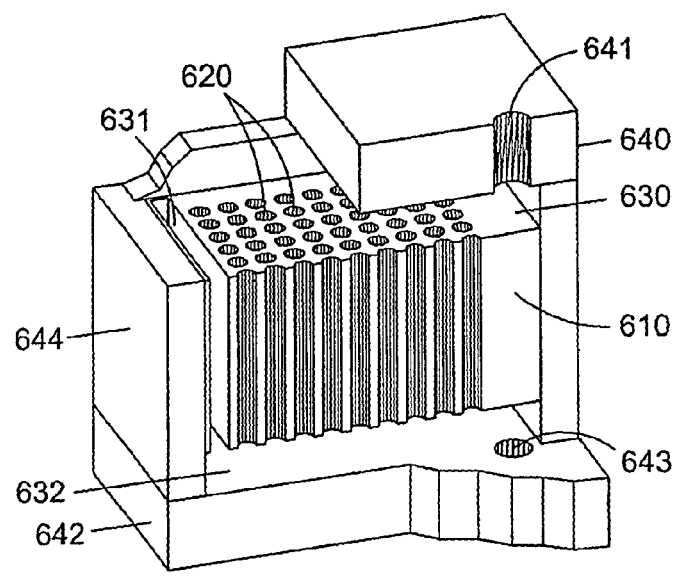
FIG. 6A is an exploded perspective view of a capillary array device containing a bypass channel that embodies the present invention.
Figure 6B:
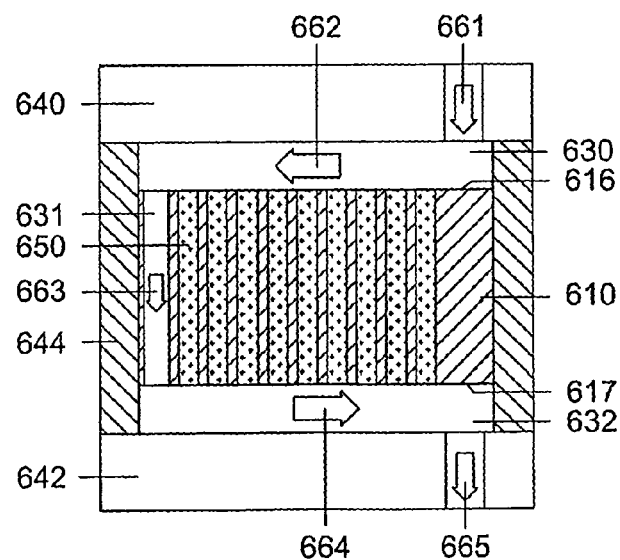
FIG. 6B schematically illustrates a cross-section view of the capillary array device of FIG. 6A and the flow path of the second fluid.

FIG. 6A is a schematic representation of the structure of yet another preferred fluidic device embodiment of the present invention. The device is composed of a fluidic template 610, a side enclosure 644, a top enclosure 640, and a bottom enclosure 642. The fluidic template 610 contains a plurality of capillary chambers 620 and a bypass channel 631. There are inlet and outlet holes 641 and 643 on the top and the bottom enclosures 640 and 642, respectively for delivering a liquid into and out of the device. The operational principle of this fluidic device embodiment is similar to what is described in the above paragraphs. In one illustrative embodiment the first fluid is an aqueous solution, the second fluid is a gas; the internal surface of the capillary chambers 620 is hydrophilic; the top surface 616 and the bottom surface 617 of the fluid template 610 are hydrophobic; and the cross-section area of the bypass channel 631 is much larger than that of capillary chambers 620. As shown in FIG. 6B, after the device is filled with the first fluid 650, the second fluid 661 is sent in through an inlet hole 641. Inside the device, the second fluid replaces the first fluid in top gap 630, the bypass channel 631, and the bottom gap 642 while leaving the first fluid 650 isolated inside the capillary chambers 620.

In a preferred embodiment, the fluidic template 110 of FIG. 1A is made of silicon material and is formed using fabrication processes, such as photolithography, etching, and coating, which are well-know to those skilled in the art of microfabrication (Madou, M., Fundamentals of Microfabrication: The Science of Miniaturization, Second Edition, CRC Press, New York, (2002)). In one aspect of the present invention, the surface of the fluidic template 110 is preferably coated with silicon dioxide, which can be made by either oxidation or evaporation during a fabrication process.

In another preferred embodiment, the fluidic template 110 is made of plastic materials, including but not limited to polyethylene, polypropylene, polystyrene, polycarbonate, polydimethylsiloxane, polyamide, polymethylmethacrylate, polyoxymethylene, epoxy, polyvinylidine fluoride, and polytetrafluoroethylene. A plastic fluidic template 110 can be made using a fabrication process selected from or combined of molding, embossing, casting, laser abolition, and mechanical machining methods, which are well-know to those skilled in the art of plastic processing as described by Becker et al. in "Polymer microfabrication methods for microfluidic analytical applications". Electrophoresis 21, 12-26 (2000) and the references therein. The use of plastic materials often has the advantage of low cost and ease of production.

Varieties of other materials, such as ceramic, glass, metal and composites of two or more materials, and corresponding fabrication processes, such as molding, embossing, casting, and any other appropriate methods, may also be used to make the fluidic template 110.

The capillary fluidic template 610 shown in FIG. 6A can be made from silicon material by a high aspect ratio etching process using commercial equipment such as ASE etching system supplied by Surface Technology Systems, Newport, UK. Anisotropic etching using wet chemistry can be used to make the capillary fluid template 610 on silicon substrates as well. The capillary fluidic template 610 can also be made from glass materials using ultrasonic drilling, laser drilling, selective etching, and any other appropriate fabrication processes that are well-known to those skilled in the art of microfabrication. Metallic materials, such as nickel, titanium, stainless steel, and various alloys, may be used to make the capillary fluidic template 610. Metallic capillary fluidic template 610 may be fabricated using electroforming, photochemical etching, and any other appropriate methods.

In one aspect of this invention, the cover plate 140 of FIG. 1A is a flat and transparent plate. The use of a transparent cover plate 140 is required when a chamber array device shown in FIG. 1A is used as a multiplexing photochemical reactor or as an assay device involving photo-detections. When a fluidic template 110 is made of Si, the cover plate 140 is preferably made of glass, which is anodically bonded to the Si fluidic template 110. Exemplary glass materials include but not limited to Corning 7740 (from Corning Incorporated, Corning, N.Y. 14831) and Borofloat® (from Schott Corporation, Yonkers, N.Y. 10701). Plastic materials can also be used to make the cover plates 140. Plastic cover plates 140 can be attached to fluidic templates 110 using an appropriate bonding processes selected from but not limited to gluing, heating, laser welding, and lamination which are well-known by those skilled in the art of plastic processing.

In another aspect of this invention, the cover plate 140 contains structural features that are not shown in FIG. 1A. For example, chambers 120 shown in FIG. 1A may be made on the cover plate 140. In this case, the cover plate 140 becomes the second fluidic template to make up a complete fluidic structure after combining the cover plate 140 with the fluidic template 110.

The selective coating of interior surfaces of the fluidic structures of the disclosed devices with films of different affinities can be achieved using various methods that are familiar to those skilled in the art of surface chemistry and microfabrication. In one illustrative silicon-based fabrication process, the silicon fluidic template 110 of FIG. 1A is first coated with silicon dioxide using an oxidation process. Then, the surface is coated with photoresist. Uniform coating of photoresist on a substrate containing deep micro-structures can be achieved using a spray coater, such as AltaSpray coater from SUSS MicroTec, Munich, Germany. Photolithography is performed to remove the photoresist from the interior surface of channels 130 while keeping the chambers 120, inlet conduits 121, and outlet conduits 122 covered with the photoresist film. The exposed channel 130 surfaces are then coated with a hydrophobic film by dipping the silicon template into an alcohol solution of a fluorinated silane compound. When the photoresist film is removed with acetone the exposed silicon dioxide interior surfaces of chambers 120 and conduits 121 and 122 are hydrophilic. Srivannavit et al. described a method of selective coating of hydrophobic films in "Design and fabrication of microwell array chips for a solution-based, photogenerated acid-catalyzed parallel oligonucleotide DNA synthesis", Sensors and Actuators, Volume 116, Issue 1, 4 Oct. 2004, Pages 150-160.

Other hydrophobic materials and processes may be applied for selective coating of hydrophobic films. In a preferred embodiment, Cytop (from Asahi Glass Company, Japan), which is a highly hydrophobic fluorinated polymer, is coated on a flat substrate using spin-coating and on a patterned substrate using dip-coating. In another preferred embodiment parylene is coated using vapor-phase deposition method. Photolithography is used either for selective etching of the polymer films or selective opening of protected areas using a lift-off process. These polymer coating and photolithographic patterning processes are well-known to those skilled in field of microfabrication.

In another preferred embodiment of the present invention, a fluorinated film is coated using gas phase deposition. The deposition can be performed in a DRIE (deep reactive ion etching) instrument, which can be used to make fluidic structures of the disclosed device on silicon substrate. A fluorocarbon polymer film can be produced in the instrument using octafluorocyclobutane-generated plasma. The fluorocarbon polymer film is a highly hydrophobic film. The use of this film may simplify the fabrication process of the disclosed device by simply depositing the film at the end of channel etching process to be performed in the same instrument. The deposition process and the instrument are well-known to those skilled in the field of microfabrication.

In yet another preferred embodiment of the present invention, a hydrophobic film is formed by chemical synthesis. In an exemplary synthesis process, PGA (photogenerated acid) is used to achieve selective chemical synthesis inside the disclosed device (a complete device having a cover plate 140 bonded to a fluidic template 110 as shown in FIG. 1A). Details of the PGA process are described by Gao et al. in U.S. Pat. No. 6,426,184, which is incorporated herein by reference. In the process, the entire interior surface of a disclosed device is first derivatized with an amine linker, on which an acid labile compound, such as boc-glycine, is coupled. Then the device is filled with a PGAP (photogenerated acid precursor) and chamber regions are exposed with light to remove the boc-protection groups on the interior surfaces of the chambers, while leaving the boc-glycine on channel surfaces intact. A base-labile compound, such fmoc-glycine, is coupled to the deprotected glycine on the interior surfaces the chambers. An acid, such as TFA (trifluoro acetic acid), is then used to remove the boc-protection group on the surface of the channels, while keeping the fmoc-protected diglycine on the chamber surfaces intact. A perfluoro-carboxylic acid, such as heptadecafluorononanoic acid, is coupled to the deprotected glycine on the interior surfaces of the channels to make the surfaces hydrophobic. The fmoc-protected interior surfaces of the chambers can then be activated for further synthesis of oligonucleotides, peptides, and other appropriate biological and chemical compounds. The use of the above specific process and chemical compounds should be viewed as an example only. Many modifications and variations of the process and substitutions of the compounds can be readily made by those skilled in the art of organic chemistry without deviating from the teaching of the present disclosure.

To complete the fabrication of the disclosed device, a cover plate 140 is attached to a fluidic template 110 as shown in FIG. 1A. Anodic bonding process can be used to attach a glass cover plate to a silicon fluidic template. When a hydrophobic film is required on the interior surfaces of channels, the channel areas of the glass cover should be selectively coated with the hydrophobic film. When the hydrophobic film is made of a monolayer of perfluoro molecules derived from fluorinated silane compound, the bonding temperature is preferably below 400° C. and the bonding is preferably performed under a protected environment of either an inert gas, such as nitrogen and/or argon, or vacuum. When the hydrophobic film is made of a polymer, such as Cytop or parylene, a thermal bonding process is preferred. Both anodic and thermal bonding processes are well-know to those skilled in the art of microfabrication.

While there is no fundamental limitation on the size of the fluidic structures of the present invention, the preferred distance between the centers of adjacent chambers is in the range of 1 to 5,000 μm. More preferably, the distance is in the range of 10 to 2,000 μm. Yet more preferably, the distance is in the range of 10 to 500 μm. Even more preferably, the distance is in the range of 10 to 200 μm. Depending on the application of the disclosed device, a preferred number of chambers in each device is above 10. Another preferred number of chambers in each device is above 100. Another preferred number of chambers in each device is above 1,000. Another preferred number of chambers in each device is above 10,000. Yet another preferred number of chambers in each device is above 30,000.

A preferred application embodiment of the present invention is multiplexing bio assay, including but not limited to real-time PCR, hybridization, immunoassay, ELISA, and peptide or protein binding assay. The present invention provides novel devices and methods for achieving a significantly increased degree of multiplexing for these assays as compared to the currently available technologies.

Real-time PCR is a bio assay method known to those skilled in the art of molecular biology (C. A. Heid, J. Stevens, K. J. Livak, P. M. Williams, (1996) Real time quantitative PCR. Genome Res. 6, 986.). The devices of the present invention can be used for real-time PCR assay. In the methods of the present invention wherein the devices are used for real-time quantitative PCR the cover plate 140 of FIG. 1A is preferably transparent. Each chamber 120 is first deposited with a pair of sequence specific primers. For some assays, such as Taqman real-time PCR, a probe is also needed in the chamber 120. Methods of primer and probe deposition are described in the flowing paragraphs. After the deposition of primers in the chambers a sample solution containing sample DNA or RNA sequences, polymerase enzymes, dNTP (deoxyribonucleotide triphosphate), and other necessary reagents useful in a PCR reaction, are injected into the fluidic device. Once the sample solution makes its way into the chambers, the sample solution is isolated with individual chambers by injecting an isolation fluid into the device. The isolation fluid can be a hydrophobic liquid or an inert gas. Isolation prevents the diffusion or exchange of molecules among individual chambers during the subsequent thermal cycling PCR reaction. Then the real-time PCR reaction is performed in a way that is essentially the same manner as a regular real-time PCR process.

The thermal cycling for the PCR reaction may be performed using a Peltier thermoelectric device with thermal couple or thermistor sensors for temperature measurement and feedback control. Mercury or Xenon lamps equipped with proper filters, lasers, or LEDs can be used as the light source for the excitation of fluorescence dyes. Photomultiplier and CCD can be used to detect the emissions from the fluorescence dyes. Laser scanning instruments or their variations that have been used for collecting fluorescence images from DNA and other microarrays can be used for collecting fluorescence images from the fluidic devices of the present invention. The instrumentation and the performance of real-time PCR process are well-know to those skilled in the art of analytical instrumentation and molecular biology.

Figure 8:
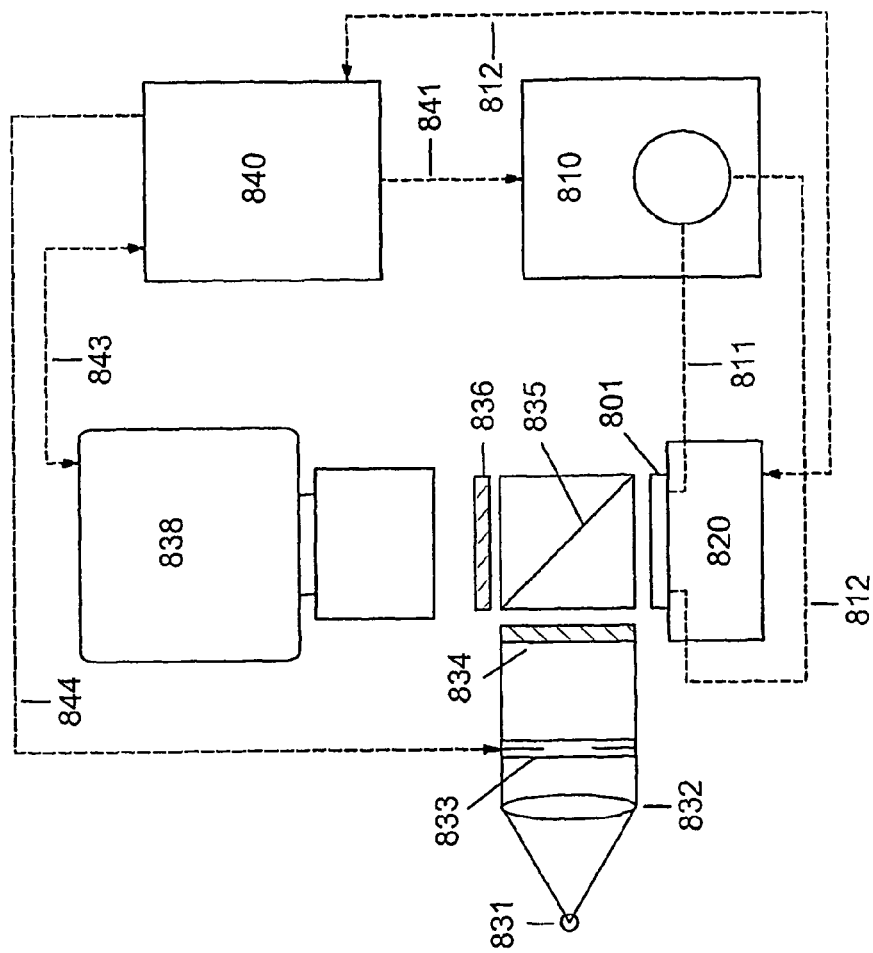
FIG. 8 is a schematic diagram of a real-time PCR detection system.

FIG. 8 illustrates an exemplary real-time PCR system for performing fluidic circulation, thermal cycling, and optical detection. The system consists of a fluid station 810 for injecting samples/PCR mix and isolation fluid into a microfluidic array device 801 of the present invention, a Peltier thermoelectric heating/cooling unit 820 for performing thermal cycling on the microfluidic array device 801, a filtered illumination system for exciting fluorescence dyes inside the microfluidic array device 801, a cooled CCD camera 838 for detecting fluorescence emission from the microfluidic array device 801, and a computer controller 840. The fluidic station 810 delivers and circulates fluids to the microfluidic array device 801 through tubing 811 and 812. For the filtered illumination system, a mercury lamp 831 can be used. The optical excitation/detection system includes a condensing lens 832, a shutter 833, an excitation filter 834, a dichroic filter 835, and an emission filter 836. The selection of proper filters is well-known to those skilled in the art of fluorescence imaging. For example, for SYBR Green I and FAM excitation and detection one may select a bandpass filter with a center wavelength at 475 nm as excitation filter and a bandpass filter with a center wavelength at 535 nm as emission filter. In another preferred embodiment of the present invention, a blue LED (light-emitting diode) based illumination system is used to replace mercury-based lamp. In yet another preferred embodiment, a laser-photomultiplier based scanning detection system is used.

Various methods that are well-known to those skilled in the art of microarrays can be used to deposit primer and probe nucleotides into the chambers. Two methods are spotting and in situ synthesis. For spotting, primer and probe nucleotides may be either covalently bound to a substrate surface or non-covalently deposited to the substrate surface. For the non-covalently deposited primers and probes, measures should be taken to prevent the molecules from being washed away from reaction chambers when a PCR mix solution is being filled into the chambers. One method for preventing escape of primers and probes from the chambers is to mix the primers and probes with an agarose gel, preferably an ultra-low gelling temperature agarose, so that the primer or probe oligos will not be washed away by the PCR mix solution and will become available in solution phase for the PCR reaction when the device is heated up. In a preferred embodiment of the present invention, the spotting method is applied to the capillary array device shown in FIG. 6A.

For the covalently bound primer and probe nucleotides are used, it is preferred that these surface bound molecules contain cleavage sites so that they can be cleaved from substrate surface before or during a PCR reaction. In a preferred embodiment of the present invention, the cleavable sites include enzymatically cleavable moieties, chemically cleavable moieties, and photochemically cleavable moieties. Enzymatically cleavable moieties include but not limited to ribonucleotides which can be cleaved by RNase A. Chemically cleavable moieties include but not limited to disulfide group which can be cleaved by DTT (DL-dithiothreitol). Photochemically cleavable moieties include but not limited to 1-(2-nitrophenyl)-ethyl, which can be incorporated into oligonucleotides during oligo synthesis using PC biotin phosphoramidite or PC amino-modifier phosphoramidite available from Glen Research (Virginia, USA). The primer nucleotides preferably have 3'-OH groups and are covalently attached to substrate surfaces at 5' ends which preferably contain amino or biotin groups for facilitating attachment chemistry. The attachment process and chemistry of oligonucleotides to solid surfaces are well-known to those skilled in the art of making DNA microarrays using spotting methods and can be used for attaching the oligonucleotides to the devices of the present invention (Mark Schena, DNA Microarrays: A Practical Approach, Oxford University Press, 1999).

Figure 7:
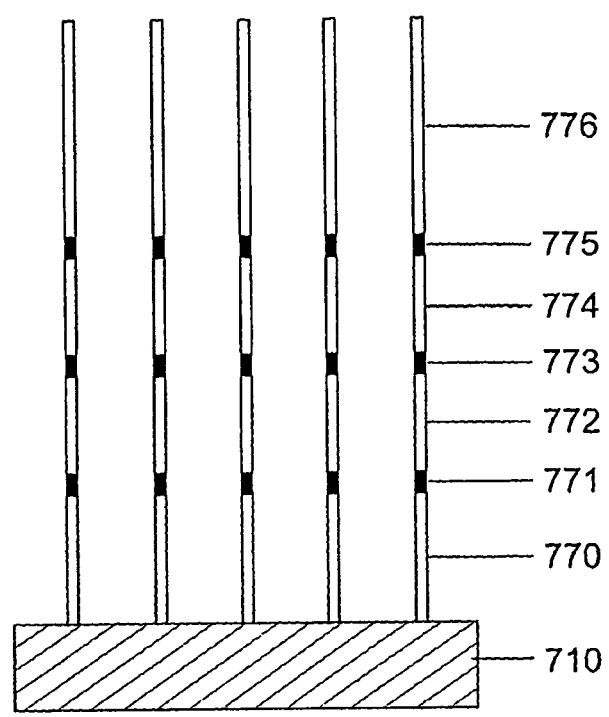
FIG. 7 is a schematic diagram of immobilized oligonucleotides containing multiple segments.

In the most preferred embodiment of the present invention, primer and probe oligo nucleotides are in situ synthesized on the interior surfaces of chambers. The in situ synthesis of oligonucleotides in the disclosed microfluidic device is preferably performed by using the PGR (photogenerated reagent) chemistry and a programmable light projection system that are described by Gao et al. in U.S. Pat. No. 6,426,184, which is incorporated herein by reference. One special requirement for real-time PCR use is to have all three oligos attached to the same reaction chamber. Various synthesis strategies can be used to meet this requirement. The first strategy involves combining all three oligo segments (two primers plus one probe) into one sequence, in which the three segments are divided by a cleavable reverse U (rU) and U nucleotides as shown in FIG. 7. The total length of the combined sequence may be between 30 to 200 nucleotides, preferably between 40 to 120 nucleotides and more preferably between 60 to 100 nucleotides. Gao described a method of making and use of reverse U nucleotide in "Linkers and co-coupling agents for optimization of oligonucleotide synthesis and purification on solid supports", US Patent Application Publication 20030120035, which is herein incorporated by reference. Reverse U can be readily cleaved by RNase A. When an oligo containing two DNA oligo segments with a rU in between is subjected to RNase A, rU would be cleaved producing one DNA oligo segment containing a polymerase active 3'-OH and the other DNA oligo segment containing rU residue at 5' end.

Figure 9:
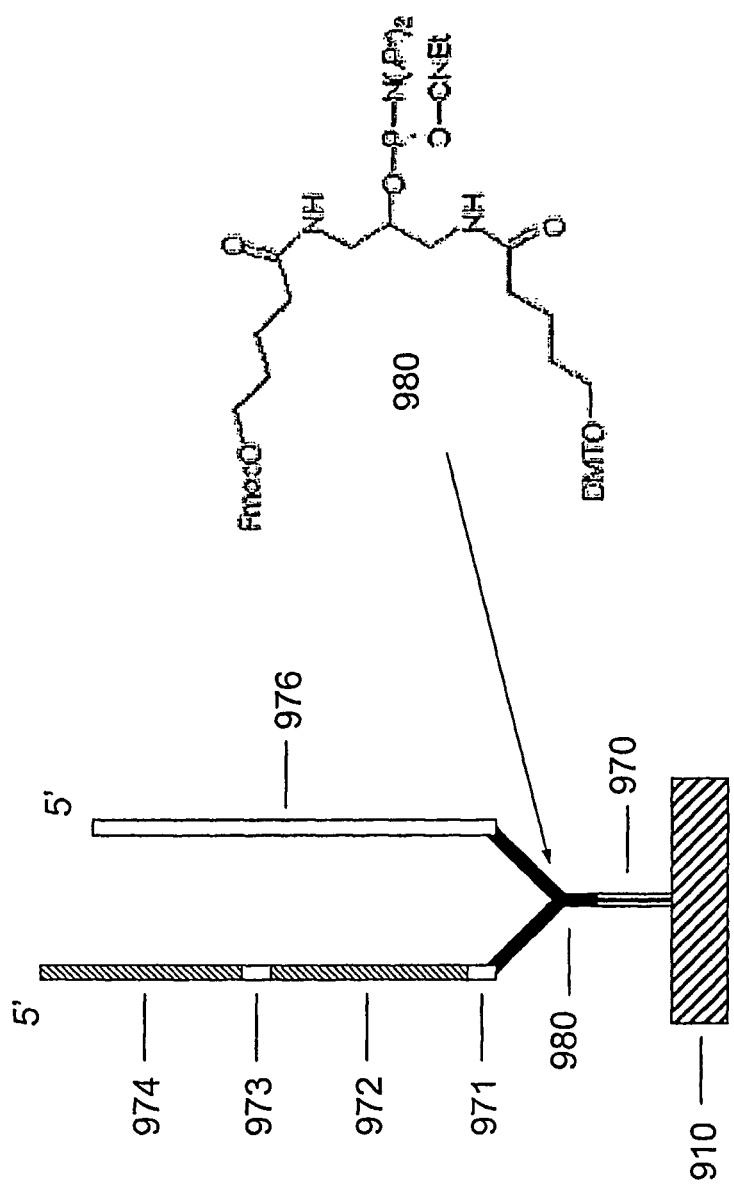
FIG. 9 schematic illustrates the orthogonal synthesis of two primers and one probe using asymmetric doubler phosphoramidite.

FIG. 9 illustrates another preferred in situ synthesis strategy. In this strategy, orthogonal synthesis is utilized make three oligo segments on one site or in one chamber. The synthesis utilizes an asymmetric doubler phosphoramidite 980 (supplied by Glen Research, Virginia, USA), which contains one acid-labile DMT protected branch and one base-labile Fmoc protected branch. On one branch, two primer-oligo-DNA segments 972 and 974 are synthesizes into one sequence with 3' ends of both segments connected rU 971 and 973. On the other branch, a probe oligo DNA 976 is synthesized.

Surface density of the in situ synthesized oligos may be controlled for achieving an optimized PCR condition. In standard real-time PCR protocols, optimal primer concentration is between 0.1 to 1.0 μM and probe concentration is about 0.05 μM. For a given chamber depth in the disclosed fluidic device (e.g. the one shown in FIG. 1A) and an RNase A cleavage efficiency, one can calculate a desired oligo surface density for producing an optimal primer concentration inside a chamber. For example, for a chamber depth of 25 μm (note: each chamber contains an upper and a lower internal surface) and an RNase A cleavage efficiency of 50%, an oligo surface density of 0.025 pmole/mm$^2$ would be needed to produce a primer concentration of 1 μM. The reduction of oligo surface density can be achieved by mixing a "terminating" phosphoramidite with a regular phosphoramidite at a predetermined ratio in the first synthesis cycle. The "terminating" phosphoramidite can be selected from a group of phosphoramidites that lack a reactive 5' moiety (for regular 3' to 5' oligo synthesis). Such phosphoramidites include but are not limited to UniCap phosphoramidite and 5'-OMe-dT, both available from Glen Research (Virginia, USA). The increase of oligo surface density can be achieved by the use of dendrimer phosphoramidite, available also from Glen Research (Virginia, USA). Obviously, this density controlling method can be applied to separately control the densities of primers and probes (in either regular or orthogonal synthesis of FIG. 7 and FIG. 9) to be optimized for real-time PCR reactions.

The methods of the present invention include a novel real-time PCR assay method utilizing the fluidic device of the present invention. This new assay method combines hybridization and PCR to achieve higher sensitivity and higher specificity when compared to standard PCR techniques. Probe molecules containing multiple segments of nucleotides are deposited or synthesized de novo on a substrate 710 surface as shown in FIG. 7. In the fluidic device of the present invention the substrate 710 surface of FIG. 7 is the interior surface of the chambers 120 of FIG. 1A. In a preferred embodiment, the probe molecule consists of three nucleotide segments, which include a forward primer 772, a reverse primer 774, and a binding probe 776. At one end of each probe molecule is a linker 770 segment through which the probe molecule is attached to the substrate 710. The three nucleotide segments are connected by cleavable sites 771, 773, and 775. The sequence design of forward primer 772 and reverse primers 774 may follow the same principles as that of regular real-time PCR such as summarized by Bustin "Absolute quantification of mRNA using real-time reverse transcription polymerase chain reaction assays", Journal of Molecular Endocrinology (2000) 25, 169-193. In a preferred embodiment of the present invention, the binding probe has a Tm (melting temperature) of about 10° C. or higher than that of primers. The linker segment 770 is selected from or a combination of alkyl, polyethylene glycol, and various other chemical linker moieties that are familiar to those skilled in the art of solid phase synthesis and microarrays. The cleavable sites 771, 773, and 775 is selected from U nucleotide, reverse U nucleotide, disulfide group and other chemical moieties that can be cleaved by enzymes, chemicals, light, and any other means that do not cause any adverse effect to PCR reactions (Gao et al. US Patent Application Publication 20030120035 and the reference therein).

In an illustrative hybridization-PCR assay embodiment of the present invention primers 772 and 774 and binding probe 776 are orientated 3' to 5'. That is the 3' end of the probe is linked to the solid support. Cleavable sites 771 and 773 are reverse U and 775 is U. When the probe is cleaved with RNase A it will produce three free standing molecules, primer 772, primer 774, and biding probe 776 in solution. PCR active 3' hydroxyl groups will be produced in primers 772 and 774 and PCR inactive 3' phosphate group will be produced in binding probe 776. In the first step in the hybridization-PCR assay process, a solution containing DNA sample sequences, which are either native DNA and derived by reverse transcription from RNA, is circulated through the fluidic device at a temperature in which the sample sequences complimentary to respective binding probes 776 can hybridize to the binding probes 776 and are retained in the corresponding chambers while non-specific sample sequences are not retained. A brief wash with an appropriate buffer solution will then be applied to the fluidic device preferably at a reduced temperature to wash the non-specific sample sequences out of the device while keeping the hybridized sample sequences in the chambers. This washing step improves the specificity of the following PCR assay. A PCR mix based on SYBR Green I double-stranded DNA binding dye assay, such as Brilliant QPCR mix by Stratagene (California, USA) is then be injected into the device. In a preferred embodiment RNase A is used to cut the cleavable sites 771, 773, and 775 and release primers 772, and 774 and binding probe 776 into solution. To avoid premature enzymatic cleavage, chip temperature is preferably kept low (e.g. at 4° C.) when the RNase A containing PCR mix is injected into the device. An isolation fluid is then injected into the chip to isolate all the chambers and the real-time PCR reaction is carried out. The hybridization process enriches specific sample sequences into corresponding small chambers and therefore significantly increases the assay sensitivity. Non-specific sequences are washed out of the chambers thereby reducing the chance for mis-priming during PCR and increase assay specificity. In a preferred embodiment of the methods of the present invention, the 3' ends of binding probes 776 are blocked so that the binding probe do not become PCR primers during PCR reaction.

It should be noted that the disclosed fluidic devices are capable of carrying out standard real-time PCR assays, in which the pre-PCR hybridization step may not be necessary. In a standard PCR assay, sample sequences can be incorporated into a PCR mix and injected into the disclosed fluidic devices. The fluidic device of the present invention may also be used to perform isothermal amplification reaction which has the advantage of requiring a simpler heating instrument as compared to conventional thermal cycling PCR instrument. Such a reaction is described by Van Ness at al. in PNAS 100, 4504 (2003).

Those skilled in the art of molecular biology should be able to map out an operational window of the real-time PCR device and associated assay protocols. Among the variable parameters are the primer and probe densities, the order of primer/probe in the combined sequences (FIG. 7 and FIG. 9), and the geometry of the chambers. Depending the materials to be used for the construction of the disclosed fluidic devices, it may be beneficial or even necessary to add one or a combination of blocking reagents, such as BSA (bovine serum albumin), PEG (polyethylene glycol), and/or PVP (polyvinylpyrrolidone).

Another preferred application of the present invention is parallel assays involving chemiluminescence and/or bioluminescence, such as ELISA and hybridization. In these applications, a solution containing enzyme(s) (such as horseradish peroxidase) attached target samples (antibody, protein, DNA, or RNA) are circulated through a microfluidic array device of this invention that contains probes (peptides, DNA, or RNA). A substrate solution containing luminol, hydrogen peroxide, and an enhancer is then injected into the microfluidic array device. An inert gas, such as nitrogen, helium, or argon, is then passed through the channels of the microfluidic array device so as to isolate reaction chambers. Chemical luminescence signal is then collected using a cooled CCD camera or a photomultiplier-based measurement instrument. The reaction-chamber isolation mechanism offered by this invention eliminates the diffusion of substrate during chemiluminescence reaction.

Another preferred application of the present invention is multiplexing of chemical reaction and/or chemical synthesis. The present invention provides improvements over earlier disclosed technologies, such as the one disclosed by Zhou in PCT WO 0202227, by introducing a new and simple isolation mechanism. In one aspect of the present invention, photogenerated reagents in solution phase and projected light patterns are used to facilitate chemical reactions in a plurality of selected chambers 220 of 2A simultaneously. The method and the apparatus relating to the use of the photogenerated reagents are described by Gao in U.S. Pat. No. 6,426,184. One important aspect of the method is a requirement to confine active photogenerated reagents inside individual chambers 220 of FIG. 2A so as to prevent the active reagents from going from a light-exposed chamber into neighboring chambers due to diffusion effect. The use of bypass channels in the present invention permits a static isolation of reaction solution inside reaction chambers. In one illustrative embodiment of the present invention, a solution containing photogenerated reagent precursor is first injected into a fluidic device, such the one shown in FIG. 2A, of this invention. An inert gas, such as helium, is then sent into the device to push the solution out of distribution, transport, and bypass channels 271, 272, 230, 231, 232, and 233 so as to isolate the solution inside the chambers 220. A selected number of chambers 220 are then exposed to light so as to generate activate reagents inside the exposed chambers 220. After a period of time that is sufficient for the completion of the intended chemical reactions inside the chambers 220, a wash solution is sent into the device to flush the active reagents out the device. This new isolation mechanism is particularly useful for those applications that require extended reaction time after the photogenerated active reagents are generated by light. The fluidic device of the present invention may be used to synthesize microarrays of various chemical and biochemical molecules, including but not limited to DNA, RNA, peptide, carbonhydride, and the combination of the above molecules.

Another advantage of the present invention is the ease of bubble and particle removal from the disclosed microfluidic array devices. For most of applications, the bypass channels 231 and 232 of FIG. 2 have significantly larger cross-sections than that of inlet and outlet conduits 221 and 222. These bypass channels, therefore, provide easier paths for particles and bubbles to be flushed out the device.

In another aspect of this invention, the cover plate 140 is a flat and opaque or translucent plate. The optical transparency of the cover plate 140 is not necessary when a chamber array device shown in FIG. 1A is to be used as a multiplexing reactor for non-photochemical reactions and a non-photo-detection based assay device. Non-photochemical reactions include electrochemical reactions, which have been described by Montgomery in U.S. Pat. No. 6,444,111. By adding electrodes to the chamber array device, one skilled in the art of electrochemistry may perform multiplexing synthesis reactions. An exemplary non-photo-detection based assay is the electron transfer based nucleic acid detection, which is described by Meade et al. in U.S. Pat. No. 6,013,459 and the references therein. By adding electrodes in a chamber array device, one skilled in the art of molecular electronic detection may perform multiplexing nucleic acid and other molecular detection.

Another preferred variation of the present invention is the use of a microwell plate to perform hybridization-PCR assay. In a preferred embodiment a microwell plate contains a plurality of microwells of 1 to 500 microns in diameter and 1 to 500 microns deep. The plate can be made of glass, silicon, plastic, and any other appropriate materials. The fabrication of such a plate is well-know to those skilled in the art of microfabrication (Gao et al. U.S. Pat. No. 6,426,184). In a preferred embodiment, the microwell plate is assembled with an enclosure to form a fluidic device which contains inlet and outlet to allow fluids to be injected and/or circulated. An exemplary make and use of a glass-based microwell plates is described by Leproust et al. in "Digital light-directed synthesis. A microarray platform that permits rapid reaction optimization on a combinatorial basis", J. Comb. Chem. 2, 349-354 (2000). For real-time PCR application, the bottom of the wells is covalently deposited with probe molecules containing primers and binding probes. In a preferred embodiment, the interior surface of the microwells is hydrophilic and the outside surface of the microwells hydrophobic. In an illustrative assay process, a solution containing DNA sample sequences is first circulated through the fluidic device at a proper temperature so that those sample sequences complimentary to respective binding probes would be hybridized and retained in the corresponding microwell while non-specific sample sequences would not be retained. A brief wash with a suitable buffer solution will then be applied to the fluidic device at a reduced temperature to wash the non-specific sample sequences out of the device while keeping the hybridized sample sequences in the microwells. A PCR mix based on SYBR Green I double-stranded DNA binding dye assay is then be injected into the device. As described in the above paragraphs, the PCR mix contains RNase A or other appropriate cleavage reagents. To avoid premature cleavage, chip temperature will be kept low (e.g. at 4° C.) when the PCR mix is injected into the device. An isolation fluid, such as oil or an inert gas, is then injected into the chip to isolate all the microwells and real-time PCR reaction is carried out thereafter.

Another alternative form of microwell plates is to facilitate a different isolation mechanism. Each microwell has an extruded lip. The microwells can be sealed or isolated by pressing an elastomer sheet or a laminate film having an adhesive coating against the microwells. The extruded lip helps the seal. The elastomer and the laminate film can be selected from various materials that are compatible with the temperatures used in PCR processes, chemically inert, and of low fluorescence.

Another aspect of the present invention is the use of beads within the fluidic device to significantly increase the synthesis capacity of the device for parallel synthesis applications. In a preferred embodiment the beads are made of high-loading substrate materials including but not limited to partially crosslinked and functionalized polystyrene beads, crosslinked polystyrene-PEG copolymer beads, CPG, and various other commonly used and specialized resin material used in solid phase synthesis. In a preferred embodiment, all beads are substantially spherical and of narrow size distribution. A fluidic device similar to that shown in FIG. 2A, except the structure of the reaction chambers, is used. In one aspect of the present invention the outlet side of each reaction chamber contains a barrier to stop beads from passing through and allow liquid to flow through. The bypass channels should be wide enough to allow beads to pass through so as to avoid plugging of the transport channels by the beads. Before loading the beads into the reaction chambers, the beads are suspended in a liquid having substantially the same density as that of the beads (excluding the void inside the beads). Then, the bead suspension liquid is circulated through the fluidic device till all the reaction chambers are filled with the beads. The process of using the bead-loaded fluidic device for chemical synthesis is similar to that of a regular device as what is described in the above paragraphs.

Figure 10:
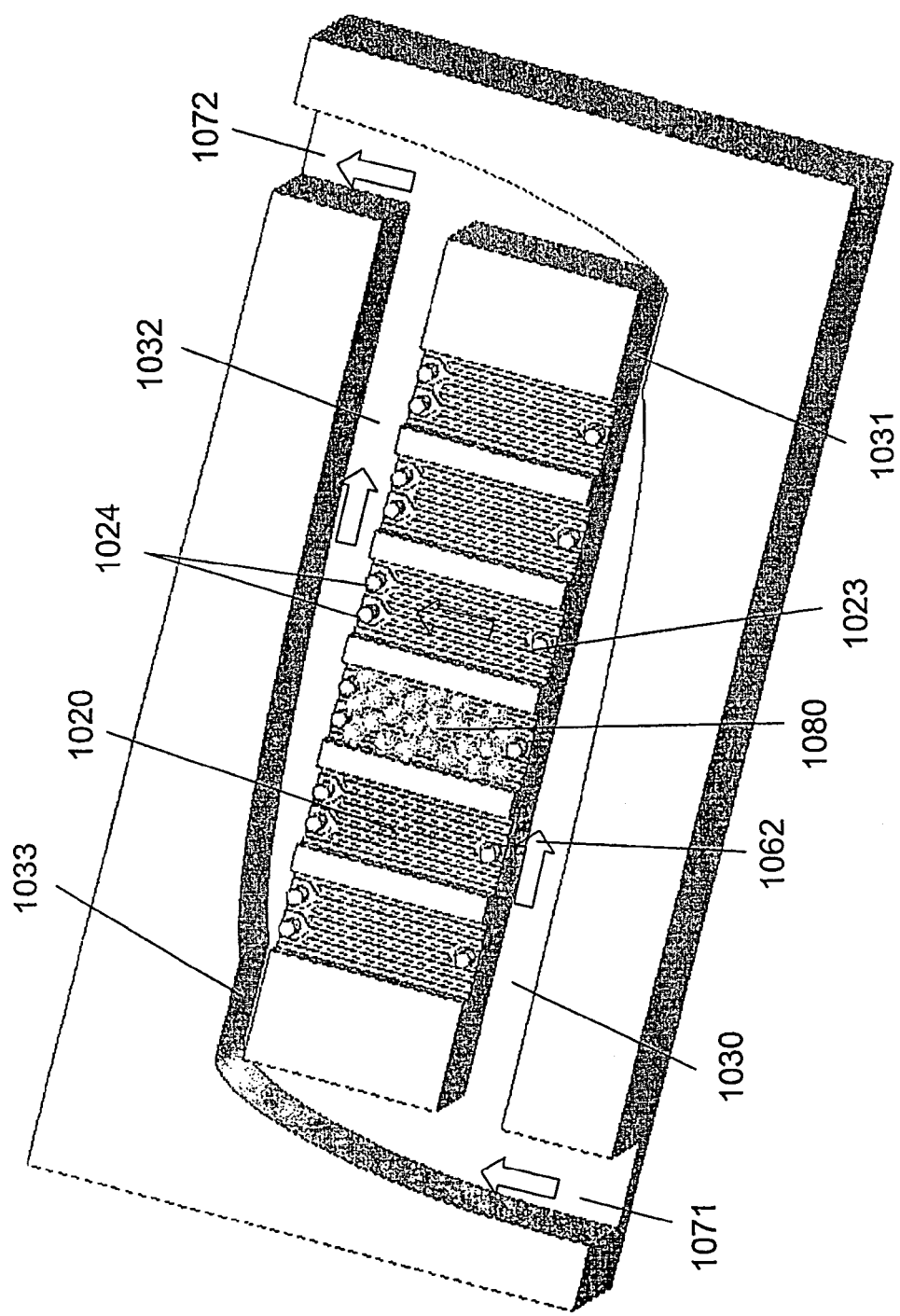
FIG. 10 is a schematic illustration of the structure of a chip designed for performing parallel synthesis on a bead substrate. For illustration purposes, beads are displayed in only one reaction chamber.

FIG. 10 schematically illustrates a bead-containing chip. For illustration purpose, only a 1D array is shown. A 2D array, which is the format of a real chip, can be constructed by repeating the 1D structure in the y direction. During an operation, the fluid enters the chip through a main inlet channel 1071, splits and flows into inlet transport channel 1030, further splits and flows through reaction chamber 1020, merges into outlet transport channel 1032, and further merges into a main outlet channel 1072 and flows out of the chip. A portion of the incoming fluid reaches the main outlet channel 1072 through inlet or outlet bypass channels 1031 and 1033 without passing through any reaction chambers 1020 or the inlet transport channel 1030. The function of the bypass channels 1031 and 1033 will be described later. The main considerations in the design of this chip include fluid flow distribution, synthesis capacity, bead-loading mechanism, chemical and photochemical reaction efficiency, device fabrication, and production cost.

In a preferred embodiment tapered fluid channels 1030 and 1032 are used to produce a uniform flow across all reaction chambers 1020 along the channels. The shape of the channels 1030 and 1032 can be derived by using a mathematical model based on resistor networks as described earlier in this disclosure. In the most operation conditions, fluidic flow inside the device is laminar flow and the flow resistance through the channels and reaction chambers can be calculated using the established formulations in fluidic mechanics (White, F. M. "Fluid Mechanics", 3rd ed. John Wiley and Sons, (1994)).

Synthesis capacity can be determined by the quantity and the capacity of beads in each reaction chamber. The size of the beads can be between about 5 to 100 μm, preferably from about 7 to 75 μm and more preferably from about 10 to 50 μm. In a preferred embodiment, a relatively small number of beads may be used in each reaction chamber. For example, only 20 to 25 20-μm beads will be needed in each reaction chamber to produce 10 pmol of a 60-mer oligo, assuming a stepwise yield of 99% for the synthesis and 1.0 pmol loading capacity of each bead.

When a small number of beads are packed into each reaction chamber statistic variations of packing density and the consequent variations of flow resistance through the packed beads may occur among different reaction chambers. The impact of this variation to the flow rate distribution may be reduced by incorporating grooves at the bottom and the top surfaces of each reaction chamber 1080 as shown FIG. 10. These grooves will provide a constant path for fluid to flow by the beads and through the reaction chambers. The overall resistance of each reaction chamber is determined by the parallel connected "resistors" of packed beads and micromachined grooves. When the resistance of grooves is sufficiently small, the resistance variation of the packed beads would have insignificant effect to the overall resistance of the reaction chamber. The grooves also provide an anti-clogging mechanism. The function of the grooves is more than just as flow resistance reducer, they provide a critical transportation path for the delivery of reagents to the beads. The grooves produce micro-reaction conditions for the beads inside the reaction chambers similar to that in a float-bed reactor, which is commonly used for solid-phase reactions. The ultimate criteria for determining the uniformity of the reaction conditions across the chip are the consistency in quality and the quantity of the oligo products from individual reaction chambers.

Several measures can be taken to ensure beads 1080 are retained inside reaction chambers 1080 during synthesis. Fence structure 1024 may be used in preventing the beads 1080 from flowing through in the forward direction. Measures should also be taken to prevent the beads 1080 from moving backwards and fall out of reaction chambers 1020. For this, first, a forward flow direction should be maintained throughout the synthesis process so that there is no driving force for the beads 1080 to flow backwards. Second, after the beads 1080 are loaded into reaction cells 1020, a thorough wash of the chip should be performed to dislodge any loose beads at the entrance of the reaction chambers. Third, micromachined gate structures 1023 may be implemented at the entrance of the reaction chambers 1080 which would allow beads to flow in but make it difficult for beads 1080 to flow back out. One such structure, as illustrated in FIG. 10, is a cylindrical rod that narrows the entrance of the reaction chamber 1020. Other shaped objects, such as chevrons pointing outwards, would form more effective gate.

Another important fluidic structure for the microfluidic bead chip is the bypass channels 1031 and 1033 shown in FIG. 10. In a bead loading process, a bead suspension is circulated through a chip and some of the beads are carried into and accumulate inside reaction chambers 1020 along the inlet transport channels while the remaining beads are carried through the bypass channels 1031 and flushed out the chip. The circulation continues until all reaction chambers 1020 are fully filled with beads. The cross-section of the bypass channel 1031 is larger than the beads 1080 to avoid any clogging or accumulation of the beads in the transport channels 1030. For bead loading, the outlet bypass channel 1033 is not necessary. However, it provides a means to adjust fluid flow distribution. For example, during a synthesis process it is desirable to quickly flush PGA out of the outlet transport channel 1032 and an adequate amount of fluid coming through the outlet bypass channels 1033 would be helpful to increase the flow rate in the outlet transport channel 1032. Although straight bypass channels 1031 and 1033 are depicted in FIG. 10, serpentine shaped bypass channels may be used so as to increase the length of the bypass channel for reducing the fluid flow through the channel while keeping the required cross-section area for beads to pass through.

EXAMPLES

Example 1

Isolation of Chambers

A microfluidic array device is fabricated using a 500-μm thick silicon wafer as a fluidic template and a 500-μm thick glass wafer as a cover plate. Fluidic structures are similar to that of FIG. 2A. The structures include 20×6=120 circular-shaped chambers of 100 μm diameter and 15 μm deep. The inlet and outlet conduits are 12 μm wide, 15 μm deep and 40 μm long. Seven tapered transport channels are 2,400 μm long, 150 μm deep, and have a taper width ramping down from 75

μm to 72 μm. Bypass channels are 39 μm wide, 150 μm deep and 310 μm long. The fluidic structures were formed using DRIE (Surface Technology Systems plc, Newport, UK) etched. The interior surfaces of the chambers are oxidation-formed silicon dioxide on the silicon substrate side and glass surface on the glass cover side. The interior surfaces of the channels of both silicon and glass sides were coated with perfluorocarbon monolayer formed by selective coating of the surfaces with 0.5% (heptadecafluoro-1,1,2,2-tetra-hydrodecyl)triethoxysilane (Gelest, Morrisville, Pa., USA) in hexane solution. The glass cover plate was bonded to the silicon wafer using anodic bonding (EV Group, Schärding, Austria). The device also contains one inlet hole and one outlet hole of 500 μm diameter made on silicon wafer for fluid injection and circulation.

A water solution of 0.2% fluorescein (activated with ammonium) was injected into the above device using a micro peristaltic pump (Instech Laboratories, Inc., Plymouth Meeting, Pa., USA). A fluorescence image of the device was taken using a cooled CCD camera (Apogee Instruments, Inc., Auburn, Calif., USA). The fluorescence image revealed that the entire internal volume, including chambers and channels, of the device was fully filled with the fluorescein solution. A perfluorodecalin (Aldrich, Wis., USA) is then injected into the device and another fluorescence image of the device was taken using the same cooled CCD camera. The image revealed that fluorescein solution inside channel regions was completely replaced with perfluorodecalin will the fluorescein solution inside all chambers remained.

Example 2

PCR using RNase A Cleaved Oligo Primers

PCR reactions were carried out using on a MJ Research PTC-225 Peltier Thermal Cycler and in 25 μL volumes. JumpStart Taq polymerase and a companion buffer solution (Sigma-Aldrich, St. Louis, Mo., USA) were used for the PCR reactions. In the buffer solution, 200 μM dNTP, 2.5 mM $MgCl_2$ (divalent cation), and 0.05% BSA were added. A 78-mer oligo DNA of 1 pg, with the sequence showing in the following, was used as a template.

4126
AGCATAGGATCCGCGATGAGCGATCGCATGACAACGAGCTAAGTCCAGC

GATCGCAGCTGGTTTTTTGAATTCATGCGT

A composite primer that contains two rU sites and a sequence showing in the following was used. The concentration used was 2 μM.

4148
GACCACGAGCATAGGATCCG(rU)CTCGTCCGACGCATGAATTC(rU)T

TTTTTTTTT

The above components were added to all PCR tubes.

The temperature program was following: 94° C. for 60 sec, 35×(94° C. for 30 sec, 55° C. for 30 sec, 72° C. for 60 sec), 72° C. for 60 sec, hold at 4° C.

To RNase A cleavage and PCR activity, 0.1 mg/mL of RNase A was added into Tube 1. As a reference, no RNase A was added to Tube 2.

PCR products were assayed using high-resolution agarose gel. The gel result revealed a band around 90 nt for the product in Tube 1 and no product band was present for the solution in Tube 2. Additionally, a comparable band as that of Tube 1 was observed from a positive control tube which contains a pair of regular primers that have the same sequences as the two primer segments of the composite primer.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, chemistry or related fields are intended to be within the scope of the following claims.

We claim:

1. A microfluidic reaction device comprising:
   a) a plurality of chambers each having a first conduit and a second conduit;
   b) a first tapered transport channel having an interior surface, said first transport channel being in flow communication with at least one said chamber through connection with said first conduit;
   c) a second tapered transport channel having an interior surface said second transport channel being in flow communication with at least one said chamber through connection with said second conduit;
   d) a first serpentine bypass channel attached to the first tapered transport channel; and
   e) a second serpentine bypass channel attached to the second tapered transport channel.

2. The microfluidic device of claim 1, wherein the interior surfaces of said first transport channel comprise a hydrophobic film.

3. The microfluidic device of claim 1, further comprising oil in said first and second transport channels and aqueous solution in said chambers.

4. The microfluidic device of claim 1, further comprising gas in said first and second transport channels and aqueous solution in said chambers.

5. The microfluidic device of claim 1, further comprising beads in said chambers.

6. The microfluidic device of claim 1, wherein the chambers and capillary chambers.

7. A microfluidic reaction device comprising:
   (a) a plurality of chambers each having a first conduit and a second conduit;
   (b) a first tapered transport channel having an interior surface, said first transport channel being in flow communication with at least one said chamber through connection with said first conduit; and
   (c) a second tapered transport channel having an interior surface, said second transport channel being in flow communication with at least one said chamber through connection with said second conduit, wherein passing a fluid through the microfluidic device provides a volume flow rate across the plurality of chambers which is substantially uniform and wherein a first serpentine bypass channel is attached to the first tapered transport channel and a second serpentine bypass channel attached to the second tapered transport channel.

8. The microfluidic device of claim 7 wherein the flow rate variation among the chambers is 5%.

9. The microfluidic device of claim 7 wherein the flow rate variation among the chambers is 10%.

10. The microfluidic device of claim 7 wherein the flow rate variation among the chambers is 20%.

11. The microfluidic device of claim 7 wherein at least one oligonucleotide comprising a first primer and a second primer is attached to at least one chamber and wherein a first cleavable moiety is located between the first and second primer and a second cleavable moiety is located between the primers and the chamber.

12. The microfluidic device of claim 11 wherein the first and second cleavable moiety is reverse uridine.

13. The microfluidic device of claim 11, wherein the oligonucleotide further comprises one or more binding probe sequences.

14. The microfluidic device of claim 13, wherein the cross-section area of the bypass channel is substantially larger than the first conduit.

15. A symmetric microfluidic reaction device comprising:
(a) a plurality of chambers having a first conduit and a second conduit;
(b) a first tapered transport channel having an interior surface, said first transport channel being in flow communication with at least one said chamber through connection with said first conduit;
(c) a second tapered transport channel having an interior surface, said second transport channel being in flow communication with at least one said chamber through connection with said second conduit;
(d) a first serpentine bypass channel attached to the first tapered transport channel;
(e) a second serpentine bypass channel attached to the second tapered transport channel; and
(f) an inlet and outlet channel such that a fluid can be passed though the device either through the inlet or outlet channel.

16. A microfluidic reaction device comprising:
a) a plurality of chambers each having a first conduit and a second conduit wherein each chamber is surrounded by a bypass channel such that the bypass channel is in fluid communication with the first and second conduit wherein the cross-section area of the bypass channel is substantially larger than the first conduit;
b) a first tapered transport channel having an interior surface, said first transport channel being in flow communication with at least one said chamber through connection with said first conduit; and
c) a second tapered transport channel having an interior surface said second transport channel being in flow communication with at least one said chamber through connection with said second conduit.

* * * * *